(12) United States Patent
Haft et al.

(10) Patent No.: US 12,059,515 B2
(45) Date of Patent: Aug. 13, 2024

(54) BREAST MILK DISTRIBUTION SYSTEM AND USES THEREOF

(71) Applicant: Nooshee Inc., Raleigh, NC (US)

(72) Inventors: Laura Haft, Raleigh, NC (US);
William C. Brody, Raleigh, NC (US);
Heath Stephenson, London (GB);
Carl-Eiler Rodrigues, Derbyshire (GB); Hill Johnson, Charlottesville, VA (US); Dominic Moffat, East Sussex (GB); Scarlett Jenkins, London (GB)

(73) Assignee: Nooshee Inc., Raleigh, NC (US)

( * ) Notice: Subject to any disclaimer, the term of this patent is extended or adjusted under 35 U.S.C. 154(b) by 0 days.

(21) Appl. No.: 18/207,040

(22) Filed: Jun. 7, 2023

(65) Prior Publication Data

US 2023/0398271 A1    Dec. 14, 2023

Related U.S. Application Data

(60) Provisional application No. 63/423,697, filed on Nov. 8, 2022, provisional application No. 63/351,643, filed on Jun. 13, 2022.

(51) Int. Cl.
*A61M 1/06* (2006.01)

(52) U.S. Cl.
CPC ............ *A61M 1/069* (2021.05); *A61M 1/066* (2014.02); *A61M 1/067* (2021.05)

(58) Field of Classification Search
CPC ........ A61M 1/06; A61M 1/062; A61M 1/064; A61M 1/066; A61M 1/067; A61M 1/068; A61M 1/069; A61M 1/0693; A61M 1/06935; A61M 1/0697; A61M 2209/045; A61M 39/223; A61M 1/28; A61M 1/281; A61M 1/282; A61M 1/284; A61M 1/285; A61M 1/287; A61M 1/288; A61M 5/16827; A61B 13/00; A61J 1/2093; A61J 1/122; A61J 1/16
See application file for complete search history.

(56) References Cited

U.S. PATENT DOCUMENTS

| | | | |
|---|---|---|---|
| 4,323,067 A | 4/1982 | Adams | |
| 4,799,922 A | 1/1989 | Beer et al. | |
| 4,909,780 A * | 3/1990 | Ouriel | A61M 1/3627 137/625.21 |
| 6,328,709 B1 | 12/2001 | Hung et al. | |
| 7,833,190 B1 | 11/2010 | Hall | |
| 11,235,093 B1 | 2/2022 | Visconti et al. | |
| 2002/0198489 A1 | 12/2002 | Silver et al. | |
| 2004/0122358 A1 * | 6/2004 | Kent | A61B 5/4288 604/74 |
| 2007/0118078 A1 | 5/2007 | McNally et al. | |
| 2014/0053931 A1 | 2/2014 | Whitaker | |
| 2014/0076454 A1 * | 3/2014 | Kjar | B65B 3/28 141/83 |
| 2015/0328380 A1 | 11/2015 | Furrer et al. | |
| 2016/0296682 A1 | 10/2016 | Phillips et al. | |

(Continued)

FOREIGN PATENT DOCUMENTS

EP    4006456 A1 *  6/2022  ............ A61M 1/062

*Primary Examiner* — Theodore J Stigell
*Assistant Examiner* — Rachel T. Smith
(74) *Attorney, Agent, or Firm* — Foley & Lardner LLP

(57) ABSTRACT

The present disclosure provides a milk distribution system, components thereof, and methods of use thereof.

19 Claims, 7 Drawing Sheets

(56) References Cited

U.S. PATENT DOCUMENTS

| | | |
|---|---|---|
| 2018/0154055 A1 | 6/2018 | Alvarez et al. |
| 2018/0303985 A1 | 10/2018 | Pan |
| 2019/0015567 A1 | 1/2019 | Barral et al. |
| 2020/0155418 A1* | 5/2020 | Myers .................... B65D 51/28 |
| 2020/0197584 A1 | 6/2020 | Gaskin et al. |
| 2021/0252201 A1 | 8/2021 | Post et al. |
| 2022/0249750 A1 | 8/2022 | Visconti et al. |
| 2023/0405193 A1 | 12/2023 | Haft et al. |

* cited by examiner

BREAST MILK DISTRIBUTION SYSTEM AND USES THEREOF

BACKGROUND OF THE INVENTION

Many new mothers use breast pumps post-birth in order to achieve their personal milk feeding and expression goals. Breast pumps systems draw breast milk from a breast of a user and may be used to pump breast milk for later consumption by an infant, to stimulate lactation in users with low milk supply, or to relieve engorgement. Breast pumps may be manually operated, for example by squeezing a handle or operation of a foot pedal. Breast pumps may also be electrically driven by a drive unit.

On average, new mothers feed their infants more than 12 times per day, with newborn infants needing to be fed every two to three hours. Mothers may spend more than four hours each day breastfeeding, on average spending 20 minutes out of every two hours breastfeeding, interrupting work, social, and sleep schedules. The demands of breastfeeding and pumping require mothers to wake up throughout the night drastically decreasing the total hours of sleep per night a mother is able to achieve. Such sleep loss contributes to a number of conditions in women, such as mastitis and postpartum depression.

There are no commercially available milk distribution systems configured for serial breast pumping sessions without removal of a breast cup or without replacement of a reservoir in the system. Thus, there is a need for new milk distribution systems.

SUMMARY OF THE INVENTION

The present disclosure provides improved breast milk distribution systems and methods of use thereof.

The invention provides a breast milk distribution system including a manifold configured to be in fluidic communication with a breast cup, wherein the manifold comprises an inlet and a plurality of outlets; and a reservoir enclosure for housing a plurality of reservoirs that are configured to be in fluidic communication with a different one of the plurality of outlets.

In some embodiments, the breast milk distribution system further includes the plurality of reservoirs. In some embodiments, the plurality of reservoirs is from 2 to 12 reservoirs.

In some embodiments, the breast milk distribution system further includes a pressure outlet in fluidic communication with each reservoir.

In some embodiments, the breast milk distribution system further includes a pressure source in fluidic communication with the manifold and/or at least one of the plurality of reservoirs.

In some embodiments, the manifold includes a straight manifold, a right-angle manifold, a round manifold, a block manifold, a square manifold, a hex manifold, a wye manifold, or a rotating joint manifold.

In some embodiments, the manifold includes a movable member including the inlet of the manifold and a stationary member including the plurality of outlets of the manifold; wherein the movable member is configured to move and place the inlet in fluidic communication with one of the plurality of outlets at a time. In some embodiments, the movable member rotates. In some embodiments, the breast milk distribution system further includes a motor to move the inlet.

In some embodiments, each of the plurality of outlets comprises a valve. In some embodiments, the breast milk distribution system further includes a drive unit configured to open and close the valve.

In some embodiments, the breast milk distribution system further includes a fluid conduit configured to provide fluidic communication between the breast cup and the inlet of the manifold. In some embodiments, the fluid conduit includes a first one directional valve and an intersecting flush line having a second one directional valve therein, wherein the first one directional valve prevents backflow from the flush line and the second one directional valve prevents backflow from the fluid conduit.

In some embodiments, the enclosure comprises a lid. In some embodiments, the manifold is disposed in the lid of the enclosure.

In some embodiments, the breast milk distribution system further includes a pressure source.

In some embodiments, the enclosure comprises a cooling element and/or insulation.

In some embodiments, the breast milk distribution system further includes the breast cup in fluidic communication with the inlet of the manifold.

In some embodiments, the enclosure further includes a weight sensor configured to measure the weight of one or more of the plurality of reservoirs.

In some embodiments, the inlet is disposed in an alignment plate, the motion of which provides fluidic communication between the inlet and only one of the plurality of outlets.

The invention provides a breast milk distribution system including a manifold configured to be in fluidic communication with a breast cup, wherein the manifold comprises an inlet and an outlet; a reservoir enclosure for housing a plurality of reservoirs, each having a reservoir inlet; and a movable member for placing the outlet in fluidic communication with each reservoir inlet in sequence.

In some embodiments, the breast milk distribution system further includes the plurality of reservoirs. In some embodiments, the plurality of reservoirs is from 2 to 12 reservoirs.

In some embodiments, the breast milk distribution system further includes a pressure outlet in fluidic communication with each reservoir.

In some embodiments, the breast milk distribution system further includes a pressure source in fluidic communication with the manifold and/or at least one of the plurality of reservoirs.

In some embodiments, the manifold includes a straight manifold, a right-angle manifold, a round manifold, a block manifold, a square manifold, a hex manifold, a wye manifold, or a rotating joint manifold.

In some embodiments, the movable member rotates.

In some embodiments, each of the outlets comprises a valve.

In some embodiments, the breast milk distribution system further includes a drive unit configured to open and close the valve.

In some embodiments, the breast milk distribution system further includes a motor to move the movable member.

In some embodiments, the breast milk distribution system further includes a fluid conduit configured to provide fluidic communication between the breast cup and the inlet of the manifold. In some embodiments, the fluid conduit comprises a first one directional valve and an intersecting flush line having a second one directional valve therein, wherein the first one directional valve prevents backflow from the flush line and the second one directional valve prevents backflow from the fluid conduit.

In some embodiments, the enclosure comprises a lid. In some embodiments, the manifold is disposed in the lid of the enclosure.

In some embodiments, the enclosure comprises a cooling element and/or insulation.

In some embodiments, the breast milk distribution system further includes the breast cup in fluidic communication with the inlet of the manifold.

In some embodiments, the enclosure further includes a weight sensor configured to measure the weight of one or more of the plurality of reservoirs.

The invention provides a method of distributing milk from breast pumping by providing any breast milk distribution system described herein; pumping a human breast to induce milk from a first breast pumping session to flow from a nipple to the manifold via the breast cup; and providing fluidic communication between the inlet of the manifold and a first reservoir to allow milk from the first breast pumping session to flow into the first reservoir.

In some embodiments, the method further includes removing fluidic communication between the inlet of the manifold and the first fluid reservoir; pumping the human breast to induce milk from a second breast pumping session to flow from the nipple to the manifold via the breast cup; and providing fluidic communication between the inlet of the manifold and a second reservoir to allow milk from the second breast pumping session to flow into the second reservoir. In some embodiments, the time between the first and second breast pumping sessions is from 30 minutes to 240 minutes. In some embodiments, the breast cup is not removed from the human breast between the first and second breast pumping sessions.

In some embodiments, providing fluidic communication between the inlet of the manifold and the first reservoir includes opening a first valve in the manifold.

In some embodiments, providing fluidic communication between the inlet of the manifold and the first reservoir includes moving a movable member in the manifold.

In some embodiments, a subject having the human breast is moving, reclining, resting, or sleeping.

The present invention provides a breast milk distribution system, including: a breast cup configured to receive a nipple; a manifold in fluidic communication with the breast cup, wherein the manifold includes an inlet and a plurality of outlets; and a valve in fluidic communication with the manifold.

Any of the following embodiments may be applied to any other breast milk distribution system described herein.

In some embodiments, the breast milk distribution system further includes a plurality of reservoirs, wherein each of the plurality of reservoirs are configured to be in fluidic communication with a different outlet. In some embodiments, the breast milk distribution system further includes from 2 to 12 reservoirs. In some embodiments, the breast milk distribution system further includes from 4 to 6 reservoirs.

In some embodiments, each reservoir includes a pressure sensor.

In some embodiments, the breast milk distribution system further includes a pressure outlet in fluidic communication with each reservoir. In some embodiments, each pressure outlet includes a valve. In some embodiments, the pressure outlet is a breather tube.

In some embodiments, each reservoir includes an inlet in fluidic communication with a different outlet of the manifold. In some embodiments, the inlet of the reservoir is configured to open and close.

In some embodiments, the breast milk distribution system further includes a plurality of valves, wherein the inlet of each reservoir includes a valve, e.g., to seal each inlet when not being filled.

In some embodiments, each reservoir includes a lid, wherein lid includes the pressure outlet, the inlet of the reservoir, and/or the valve of the reservoir.

In some embodiments, the breast milk distribution system further includes a pressure source in fluidic communication with the breast cup, the manifold, and/or at least one of the plurality of reservoirs. In some embodiments, the pressure source is a negative pressure source or a positive pressure source. In some embodiments, the pressure source is configured to open and/close an outlet of the manifold. In some embodiments, the pressure source is configured to open and/close an inlet of a reservoir.

In some embodiments, the breast cup includes (i) a housing; (ii) a breast shield; and (iii) a diaphragm disposed between the housing and the breast shield, wherein the diaphragm is further disposed between a pressure chamber and a milk chamber. In some embodiments, the negative pressure source is fluidic communication with the pressure chamber. In some embodiments, the plurality of reservoirs is configured to be in fluidic communication with the milk chamber.

In some embodiments, the manifold includes a straight manifold, a right-angle manifold, a round manifold, a block manifold, a square manifold, a hex manifold, a wye manifold, or a rotating joint manifold.

In some embodiments, the manifold includes (i) a movable, e.g., rotating, member including the inlet of the manifold and a fluid conduit, wherein the inlet of the manifold and the fluid conduit are in fluidic communication, and (ii) a stationary member including the plurality of outlets of the manifold. In some embodiments, the movable, e.g., rotating, member is configured to move, e.g., rotate, and align the fluid conduit with each of the plurality of outlets of the manifold.

In some embodiments, the fluid conduit of the movable, e.g., rotating, member includes an outlet, and the diameter of the outlet of the fluid conduit has the same diameter as the outlets of the manifold. In some embodiments, the diameter of the outlet of the fluid conduit is larger than the diameter of the outlets of the manifold. In some embodiments, the diameter of the outlet of the fluid conduit is smaller than the diameter of the outlets of the manifold.

In some embodiments, the outlets of the manifold are radially disposed in the stationary member.

In some embodiments, the inlet of the manifold has a longitudinal axis orthogonally arranged to a longitudinal axis of each of the outlets of the manifold.

In some embodiments, each of outlets of the manifold includes a valve. In some embodiments, the valve includes a ball valve, a batch dispensing valve, a butterfly valve, a diaphragm valve, a diverting valve, a gate valve, a piston valve, a plug valve, a pinch valve, a saddle valve, a solenoid valve, a stem valve, a stop cock valve, or a three-way valve. In some embodiments, the valve is a solenoid valve. In some embodiments, the valve is a pinch valve. In some embodiments, the valve is a three-way solenoid pinch valve.

In some embodiments, the breast milk distribution system further includes a drive unit configured to open and close the valve. In some embodiments, the drive unit is a stepper motor or a linear actuator. In some embodiments, the stepper motor is attached to the manifold, wherein the stepper motor is configured to rotate the manifold. In some embodiments, the linear actuator is an electric linear actuator, a hydraulic linear actuator, or a pneumatic linear actuator.

In some embodiments, the breast milk distribution system further includes a fluid conduit providing fluidic communication between the breast cup and the inlet of the manifold. In some embodiments, the breast milk distribution system further includes a plurality of fluid conduits providing fluidic communication between each of the outlets of the manifold and the plurality of reservoirs.

In some embodiments, the plurality of reservoirs is disposed in an enclosure. In some embodiments, the enclosure includes a lid, e.g., wherein the manifold is disposed in the lid of the enclosure. In some embodiments, closure of the lid is configured to provide fluidic communication between at least one reservoir and at least one outlet of the manifold. In some embodiments, the enclosure further includes the pressure source. In some embodiments, the enclosure includes a cooling element and/or insulation.

In some embodiments, the breast milk distribution system further includes a control unit configured to (i) send a signal to the valve to open and close or (ii) send a signal to the drive unit to move, e.g., rotate the movable, e.g., rotating, member.

The present invention provides a breast milk distribution system, including: a breast cup configured to receive a nipple; and a manifold in fluidic communication with the breast cup, wherein the manifold includes an inlet and an outlet that is configured to move from a first position to a second position.

Any of the following embodiments may be applied to any other breast milk distribution system described herein.

In some embodiments, the breast milk distribution system further includes a plurality of reservoirs, wherein each of the plurality of reservoirs is configured to be in fluidic communication with the outlet of the manifold. In some embodiments, the outlet of the manifold is configured to be in fluidic communication with one reservoir at a time.

In some embodiments, each reservoir includes an inlet, and the inlet of the reservoir is configured to open and close. In some embodiments, each inlet of each reservoir includes a valve configured to open and close the inlet.

In some embodiments, each reservoir includes a pressure sensor.

In some embodiments, each reservoir includes a pressure outlet.

In some embodiments, the breast milk distribution system further includes a pressure source in fluidic communication with the breast cup, the manifold, and/or at least one of the plurality of reservoirs. In some embodiments, the pressure source is a negative pressure source or a positive pressure source.

In some embodiments, the breast cup includes (i) a housing; (ii) a breast shield; and (iii) a diaphragm disposed between the housing and the breast shield, wherein the diaphragm is further disposed between a pressure chamber and a milk chamber. In some embodiments, the negative pressure source is fluidic communication with the pressure chamber. In some embodiments, the plurality of reservoirs is configured to be in fluidic communication with the milk chamber.

In some embodiments, the breast milk distribution system further includes a drive unit configured to move the outlet. In some embodiments, the drive unit is a stepper motor or a linear actuator. In some embodiments, the manifold includes the stepper motor, and the stepper motor is configured to move, e.g., radially, the outlet of the manifold. In some embodiments, the linear actuator is an electric linear actuator, a hydraulic linear actuator, or a pneumatic linear actuator.

In some embodiments, the breast milk distribution system further includes a fluid conduit providing fluidic communication between the breast cup and the inlet of the manifold. In some embodiments, the breast milk distribution system further includes a fluid conduit providing fluidic communication between the inlet of the manifold and the outlet of the manifold.

In some embodiments, the breast milk distribution system further includes an arm, wherein the fluid conduit is disposed in and/or on the arm. In some embodiments, the arm includes an articulating arm.

In some embodiments, the plurality of reservoirs is disposed in an enclosure. In some embodiments, the enclosure includes a lid, and wherein the manifold is disposed in the lid of the enclosure.

In some embodiments, the breast milk distribution system further includes a hall effect sensor.

In some embodiments, the breast milk distribution system further includes a microswitch, e.g., to rehome the movable member.

The present invention provides a method of distributing milk from breast pumping, including: (i) providing the breast milk distribution system of the present disclosure; (ii) pumping a human breast to induce milk from a first breast pumping session to flow from a nipple to the manifold via a breast cup; (iii) providing fluidic communication between the inlet of the manifold and a first reservoir to allow milk from the first breast pumping session to flow into the first reservoir; (iv) removing fluidic communication between the inlet of the manifold and the first fluid reservoir; (v) pumping the human breast to induce milk from a second breast pumping session to flow from the nipple to the manifold via the breast cup; and (vi) providing fluidic communication between the inlet of the manifold and a second reservoir to allow milk from the second breast pumping session to flow into the second reservoir.

Any of the following embodiments may be applied to any other method of using a breast milk distribution system described herein.

In some embodiments, providing fluidic communication between the inlet of the manifold and the first reservoir includes opening a first valve. In some embodiments, the control unit sends a signal to the first valve to open and/or close. In some embodiments, the control unit sends a signal to the second valve to open and/or close.

In some embodiments, the method further includes from 30 minutes to 240 minutes (about 30 minutes to 60 minutes, about 30 minutes to 90 minutes, about 60 minutes to about 180 minutes, about 60 minutes to about 120 minutes, about 90 minutes to 120 minutes, or about 120 minutes to 240 minutes) between step (ii) and step (v).

In some embodiments, the method further includes (vi) removing fluidic communication between the inlet of the manifold and the second fluid reservoir; (vii) providing fluidic communication between the inlet of the manifold and a third reservoir; and (viii) pumping the human breast to induce milk from a third breast pumping session to flow from the nipple to the manifold via the breast cup. In some embodiments, the method further includes from 30 minutes to 240 minutes (about 30 minutes to 60 minutes, about 30 minutes to 90 minutes, about 60 minutes to about 180 minutes, about 60 minutes to about 120 minutes, about 90 minutes to 120 minutes, or about 120 minutes to 240 minutes) between step (v) and step (viii).

In some embodiments, the method further includes providing fluidic communication between (i) the inlet of the manifold and (ii) the first reservoir, the second reservoir, or the third fluid reservoir by moving, e.g., rotating, the movable, e.g., rotating, member. In some embodiments, the method further includes removing fluidic communication between (i) the inlet of the manifold and (ii) the first reservoir, the second reservoir, or the third fluid reservoir by moving, e.g., rotating, the movable, e.g., rotating, member.

In some embodiments, the method further includes providing fluidic communication between (i) the inlet of the manifold and (ii) the first reservoir, the second reservoir, or the third fluid reservoir by opening the valve to the inlet of the first reservoir, the second reservoir, or the third fluid reservoir. In some embodiments, the method further includes removing fluidic communication between (i) the inlet of the manifold and (ii) the first reservoir, the second reservoir, or the third fluid reservoir by closing the valve to the inlet of the first reservoir, the second reservoir, or the third fluid reservoir.

In some embodiments, the method further includes providing fluidic communication between (i) the inlet of the manifold and (ii) the first reservoir, the second reservoir, or the third fluid reservoir by moving the arm. In some embodiments, the method further includes removing fluidic communication between (i) the inlet of the manifold and (ii) the first reservoir, the second reservoir, or the third fluid reservoir by moving the arm. In some embodiments, the method further includes moving the arm with the drive unit, wherein the drive unit is the stepper motor.

In some embodiments, a subject including the human breast is moving, reclining, resting, or sleeping.

The present disclosure further provides a kit comprising a manifold and a plurality of reservoirs (e.g., 2 to 3, 2 to 4, 2 to 5, 2 to 6, 2 to 8, 2 to 10, 3 to 4, 3 to 5, 3 to 6, 4 to 5, 4 to 6, 4 to 8, 4 to 10, 5 to 10, 2, 3, 4, 5, 6, 7, 8, 9, 10, 11, 12, 13, 14, 15, 16, 17, 18, 19, or 20).

Definitions

To facilitate the understanding of this invention, a number of terms are defined below and throughout the disclosure. Unless otherwise defined, all technical and scientific terms used herein have the same meaning as commonly understood by one of ordinary skill in the art to which this invention belongs. The terminology herein is used to describe specific embodiments of the invention, but their usage does not limit the invention, except as outlined in the claims.

Terms such as "a", "an," and "the" are not intended to refer to only a singular entity but include the general class of which a specific example may be used for illustration.

The term "about," as used herein, refers to a value that is within 10% above or below the value being described.

The term "fluidically connected," as used herein, refers to a direct connection between at least two device elements, e.g., a channel, reservoir, etc., that allows for fluid to move between such device elements without passing through an intervening element.

The term "food contact substance," as used herein, refers to a substance or material that is intended for use as a component in manufacturing, packing, packaging, transporting, or holding food in which such use is not intended to have any technical effect in such food.

The term "fluidic communication," as used herein, refers to a connection between at least two device elements, e.g., a channel, reservoir, etc., that allows for fluid to move between such device elements with or without passing through one or more intervening device elements.

The term "valve," as used herein, refers to an element which regulates, directs or controls the flow of a fluid by opening, closing, or partially obstructing a fluid pathway.

BRIEF DESCRIPTION OF THE DRAWINGS

The following detailed description of the embodiments of the invention will be better understood when read in conjunction with the appended drawings. For the purpose of illustrating the invention, there are shown in the drawing embodiments, which are presently exemplified. It should be understood, however, that the invention is not limited to the precise arrangement and instrumentalities of the embodiments shown in the drawings.

DETAILED DESCRIPTION OF THE INVENTION

The present disclosure provides improved breast milk distribution systems, components thereof, and methods of use thereof. The present breast milk distribution systems are particularly advantageous for use in a series of breast pumping sessions without removal of a breast cup and/or without replacement of a reservoir in the breast milk distribution system.

Breast Milk Distribution System

The United States Food and Drug Administration (FDA) advises against mixing freshly expressed breast milk with already cooled or frozen milk as it can rewarm the older stored milk. The FDA also advises against storing milk at room temperature for more than 4 hours. Thus, it is advantageous to have a breast milk distribution system (1) that can provide for multiple breast pumping sessions without the removal of a breast cup (2), as well as divert milk to different reservoirs (3) from a plurality of breast pumping sessions.

The present disclosure provides a milk distribution system, e.g., a breast milk distribution system (1). The breast milk distribution system is advantageous in that it may facilitate repeated breast pumping without the removal of a breast cup (2) from a breast and/or without the replacement of a reservoir (3) from a breast milk distribution system (1). The presently disclosed breast milk distribution system (1) is advantageous in that it may be used with a variety of breast cups and breast pump systems.

Figure 1:
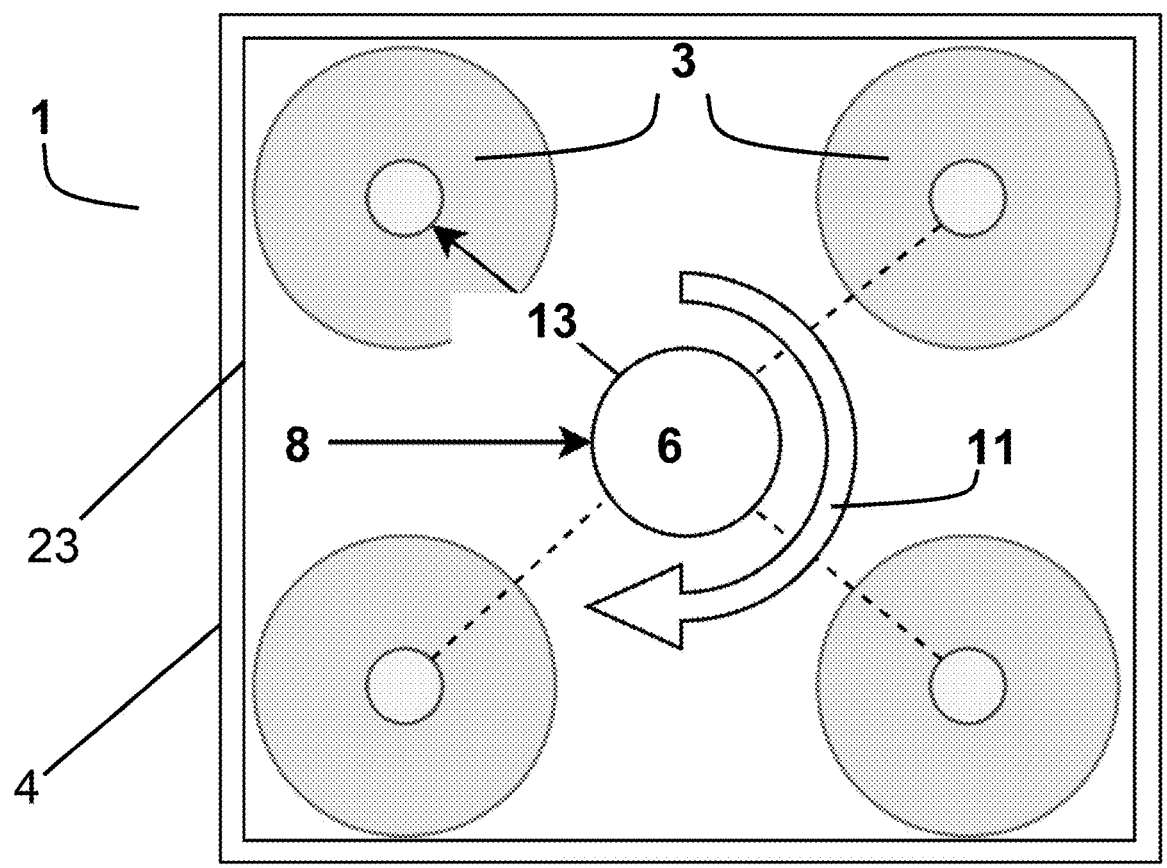
FIG. 1 shows a schematic drawing of a breast milk distribution system (1) including (i) a plurality of reservoirs (3) and (ii) a manifold (6) having an inlet (8), at least one outlet (13), and an integral drive unit (11), wherein the manifold (6) is configured to rotate to provide fluidic communication between an outlet of the manifold (13) and a reservoir (3).

In some embodiments, the breast milk distribution system (1) can include a manifold (6) comprising an inlet (8) and a plurality of outlets (13), e.g., as shown in FIG. 1. Each outlet (13) may provide fluidic communication to a different reservoir (3).

Figure 2:
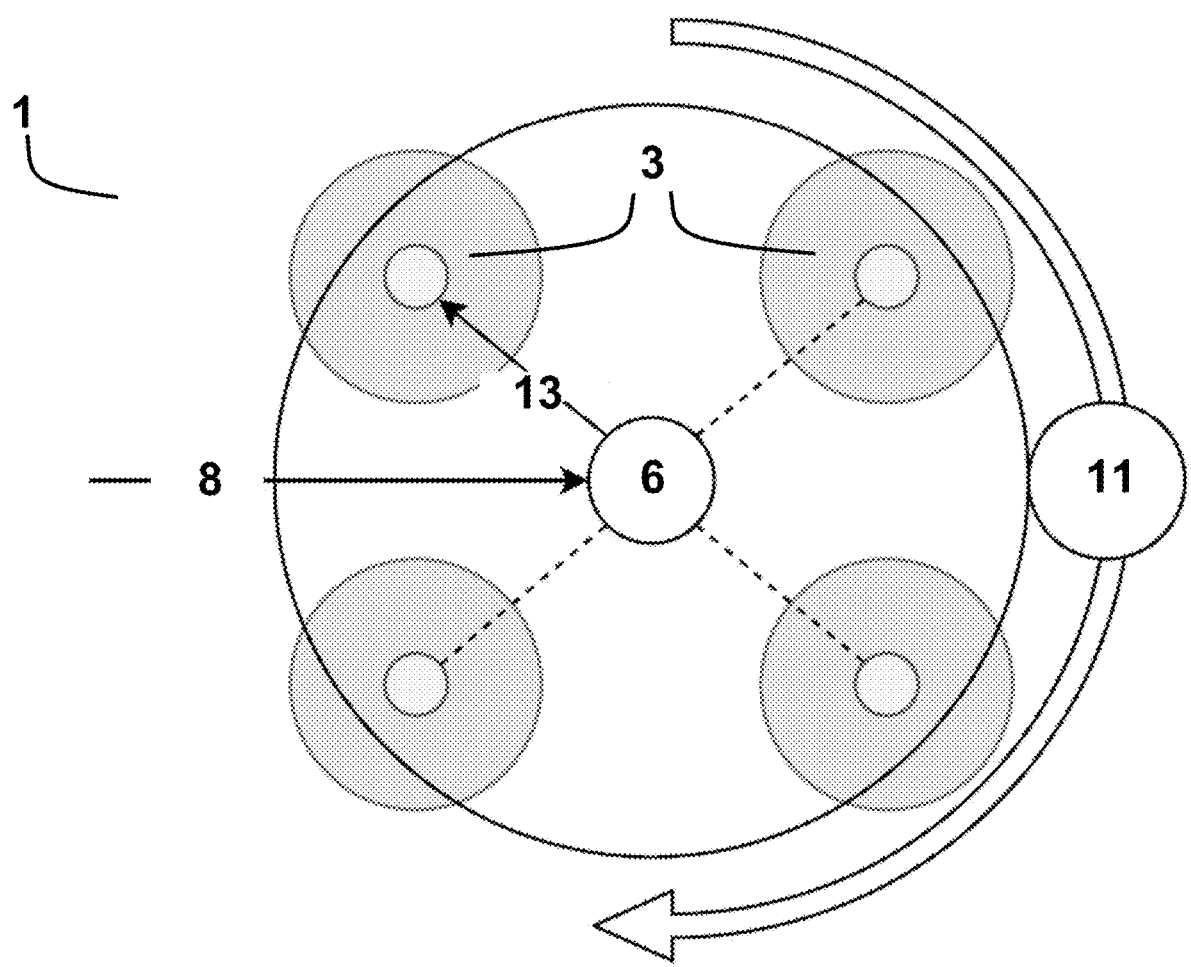
FIG. 2 shows a schematic drawing of a breast milk distribution system (1) including (i) a plurality of reservoirs (3), (ii) a drive unit (11), and (iii) a manifold (6) having an inlet (8) and at least one outlet (13), wherein the drive unit (11) is configured to rotate the manifold (6) to provide fluidic communication between an outlet of the manifold (13) and a reservoir (3).

Alternatively, the manifold (6) can include an inlet (8) and an outlet (13), in which the outlet (13) is configured to provide fluidic communication to a plurality of reservoirs (3). In some embodiments, the milk distribution system (1) includes a manifold (6) configured to be in fluidic communication with a breast cup (2), wherein the manifold (6) includes an inlet (8) and an outlet (13) configured to move from a first position to a second position, e.g., as shown in FIG. 2.

In some embodiments, the breast milk distribution system (1) includes a plurality of reservoirs (3), e.g., 1, 2, 3, 4, 5, 6, 7, 8, 9, 10, 11, 12, 13, 14, 15, 16, 17, 18, 19, or 20. In some embodiments, the breast milk distribution system (1) can include a manifold (6) comprising an inlet (8) and a plurality of outlets (13), wherein each outlet (13) comprises a valve (24); and a plurality of reservoirs (3), wherein each of the plurality of reservoirs (3) is in fluidic communication with a different outlet (13).

In some embodiments, the breast milk distribution system (1) is configured to distribute milk from a plurality of breast pumping sessions based on a pre-programmed pumping schedule input by a user. In some embodiments, milk from a first pre-programmed breast pumping session of the pre-programmed pumping schedule is transported to a first reservoir (3), and milk from a second pre-programmed breast pumping session of the pre-programmed pumping schedule is transported to a second reservoir (3). Different pumping sessions may be spaced apart by time, e.g., 3-4 hours.

Pumping milk to the milk distribution system may occur by the action of the diaphragm. Other pumping mechanisms may also be employed, including providing positive pressure breast cup, e.g., by forced air or providing negative pressure to a fluid conduit between the breast cup and a reservoir. Negative pressure may be employed by a peristaltic pump or by air being pulled into the fluid conduit. These may also act to flush the conduit after a pumping session or after a set number of pumping session. For example, a flush line may connect to the fluid conduit, with both the flush line and the fluid conduit having one directional valves to prevent back flow. Negative pressure may be applied by reducing pressure in a reservoir, and a vent may be present to release pressure when desired, e.g., FIG. 6.

Breast milk distribution systems may also include a pressure source, a reservoir enclosure, one or more fluid conduits, and/or a breast cup.

The breast milk distribution system may be employed with any suitable breast cup that can be in fluidic communication with the system, e.g., via a fluidic conduit. As is known in the art, breast cups may include a breast shield component that is designed to contact the breast and surround the nipple. Breast cups may also include a housing to surround the breast shield. The breast cup may be actuated manually or by automation, e.g., by pressure cycles from a pump or other pressure source. The system is advantageous for automated pumping as it allows for the breast cup to stay in place for multiple sessions, while allowing milk from separate sessions to be stored separately.

The breast milk distribution system may be configured such that the user may roll during rest and/or sleep. Currently available breast milk distribution systems are not designed to be utilized while resting, reclining, or sleeping.

Reservoir

The breast milk distribution system (1) may include a reservoir (3). The reservoir (3) is a collection container for the milk, such as a bottle or bag. The reservoir (3) may be polymeric or fabric. The reservoir (3) may be in fluidic communication with the negative pressure source (9), such that fluid is moved from the breast, through the negative pressure source (9), to the reservoir (3). The reservoir (3) may be releasably connected to a fluid conduit (5), such as a tube. The reservoir (3) may be configured for ease of cleaning. The reservoir (3) may be placed in a dishwasher, refrigerator, and/or freezer. In some embodiments, the reservoir (3) is insulated, e.g., with foam or a reflective material. Typically, reservoirs (3) are removable from the system, e.g., to feed an infant.

In some embodiments, the reservoir includes a volume from about 50 mL to about 1500 mL (e.g., about 50 mL to about 100 mL, about 50 mL to about 150 mL, about 50 mL to about 200 mL, about 50 mL to about 250 mL, about 50 mL to about 300 mL, about 50 mL to about 400 mL, about 50 mL to about 500 mL, about 50 mL to about 600 mL, about 50 mL to about 700 mL, about 50 mL to about 700 mL, about 50 mL to about 750 mL, about 50 mL to about 800 mL, about 50 mL to about 900 mL, about 50 mL to about 1000 mL, about 50 mL to about 1100 mL, about 50 mL to about 1200 mL, about 50 mL to about 1300 mL, about 50 mL to about 1400 mL, about 100 mL to about 250 mL, about 100 mL to about 500 mL, about 100 mL to about 750 mL, about 100 mL to about 1000 mL, about 100 mL to about 1250 mL, about 250 mL to about 500 mL, about 250 mL to about 750 mL, about 250 mL to about 1000 mL, about 250 mL to about 1250 mL, about 250 mL to about 1500 mL, about 500 mL to about 750 mL, about 500 mL to about 1000 mL, about 500 mL to about 1250 mL, about 500 mL to about 1500 mL, about 750 mL to about 1000 mL, about 750 mL to about 1250 mL, about 750 mL to about 1500 mL, about 1000 mL to about 1250 mL, about 1250 mL to about 1500 mL, about 50 mL, about 100 mL to about 150 mL, about 200 mL, about 250 mL, about 300 mL, about 350 mL, about 400 mL, about 450 mL, about 500 mL, about 55 mL, about 600 mL, about 650 mL, about 700 mL, about 750 mL, about 800 mL, about 850 mL, about 900 mL, about 950 mL, about 1000 mL, about 1050 mL, about 1100 mL, about 1150 mL, about 1200 mL, about 1250 mL, about 1300 mL, about 1350 mL, about 1400 mL, about 1450 mL, or about 1500 mL).

In some embodiments, the breast milk distribution system (1) includes a plurality of reservoirs (3). In some embodiments, breast milk distribution system includes from 1 to 10 reservoirs (3) (e.g., from 1 to 2, from 1 to 3, from 1 to 4, from 1 to 5, from 1 to 6, from 1 to 7, from 1 to 8, from 1 to 9, from 2 to 3, from 2 to 4, from 2 to 5, from 2 to 6, from 2 to 7, from 2 to 8, from 3 to 4, from 3 to 5, from 3 to 6, from 4 to 5, from 4 to 6, from 4 to 8, from 4 to 10, from 5 to 8, from 5 to 10, 1, 2, 3, 4, 5, 6, 7, 8, 9, or 10). In some embodiments, the breast milk distribution system (1) further includes from 2 to 12 reservoirs (3). In some embodiments, the breast milk distribution system (1) further includes from 4 to 6 reservoirs (3). In some embodiments, the plurality of reservoirs (3) is configured to be in fluidic communication with the breast cup.

In some embodiments, each reservoir (3) includes a lid, wherein lid includes the pressure outlet, the inlet of the reservoir (3), and/or the valve of the reservoir (3). The lid can be integral to or attached to the reservoir (3). In some embodiments, the lid is releasably attached to the reservoir (3). In some embodiments, the lid is screwed or snapped onto the reservoir (3). In particular, the reservoir (3) may include external threads, the lid may include internal threads, and the internal threads and the external threads may provide releasable attachment of the reservoir (3) and lid. In some embodiments, the lid is attached with a magnet, e.g., an electromagnet. In some embodiments, the lid is configured to be opened and/or closed with the electromagnet. In some embodiment, the lid is configured to be opened and/or closed with pressure, e.g., air pressure.

The lid of the reservoir can have a substantially flat or rounded top surface.

In some embodiments, the reservoir (3), e.g., the lid of the reservoir (3), includes a pressure outlet. The pressure outlet may or may not include a valve (24). In some embodiments, the pressure outlet is a breather tube. In some embodiments, the pressure outlet is an orifice, e.g., the reservoir (3) or the lid of the reservoir (3) may include an orifice. In some embodiments, the breast milk distribution system (1) includes a pressure outlet in fluidic communication with each reservoir (3). A pressure outlet is advantageous in allowing excess pressure to vent as the reservoir (3) is being filled with milk. In some embodiments, the pressure outlet is solely open as the reservoir (3) is being filled, and the pressure outlet is otherwise nominally closed. An outlet may be connected to a negative pressure source and a vent, e.g., to remove warm air to aid in cooling or to provide suction for milk flow.

Manifold

The breast milk distribution system (1) can include a manifold (6). The manifold may include at least one inlet (8) and at least one outlet (13). The manifold may also include at least one valve. In some embodiments, the manifold is disposed in a reservoir enclosure. In other embodiments, the manifold is in a separate enclosure.

In some embodiments, the manifold is disposed between the breast cup (2) and a plurality of reservoirs (3). In some embodiments, the manifold is disposed between two breast cups (2), and the plurality of reservoirs (3). Milk from different breast pumping sessions may be directed to different reservoirs (3), such as different breast pumping sessions in the same evening. In some embodiments, each reservoir (3) includes an inlet, wherein each inlet of the reservoir in fluidic communication with a different outlet of the manifold. In some embodiments, the inlet of the reservoir (3) is configured to open and close. Switching from a first, second, third, fourth, fifth, etc., reservoir can be manual or automatic.

In some embodiments, the manifold includes a substrate having a plurality of fluid conduits disposed therein. In some embodiments, the manifold includes a straight manifold, a right-angle manifold, a round manifold, a block manifold, a square manifold, a hex manifold, a wye manifold, or a rotating joint manifold. In some embodiments, the manifold includes a straight manifold or a right-angle manifold. In a straight manifold, fluid enters and exits the manifold in the same direction. In a right-angle manifold, fluid exits the manifold at a right angle from the direction the fluid entered the manifold.

In some embodiments, the manifold includes an inlet. In some embodiments, the manifold includes from 1 to 20 inlets (e.g., from 1 to 2, from 1 to 3, from 1 to 4, from 1 to 5, from 1 to 6, from 1 to 7, from 1 to 8, from 1 to 9, from 1 to 10, from 1 to 15, from 2 to 3, from 2 to 4, from 2 to 5, from 2 to 6, from 2 to 7, from 2 to 8, from 3 to 4, from 3 to 5, from 3 to 6, from 3 to 7, from 3 to 8, from 4 to 5, from 4 to 6, from 4 to 8, from 4 to 10, from 5 to 6, from 5 to 7, from 5 to 8, from 5 to 10, from 6 to 8, from 6 to 10, from 6 to 12, from 8 to 10, from 8 to 12, from 10 to 12, from 10 to 15, from 10 to 20, from 12 to 16, from 15 to 20, 1, 2, 3, 4, 5, 6, 7, 8, 9, 10, 11, 12, 13, 14, 15, 16, 17, 18, 19 or 20).

In some embodiments, the inlet is threaded. In some embodiments, the inlet includes internal threads and/or external threads. In some embodiments, the inlet includes a fluidic fitting. In some embodiments, the inlet includes a Luer fitting, wherein the Luer fitting may releasably connect the inlet and a fluid conduit (5).

In some embodiments, the manifold includes an outlet. In some embodiments, the manifold includes from 1 to 20 outlets (e.g., from 1 to 2, from 1 to 3, from 1 to 4, from 1 to 5, from 1 to 6, from 1 to 7, from 1 to 8, from 1 to 9, from 1 to 10, from 1 to 15, from 2 to 3, from 2 to 4, from 2 to 5, from 2 to 6, from 2 to 7, from 2 to 8, from 3 to 4, from 3 to 5, from 3 to 6, from 3 to 7, from 3 to 8, from 4 to 5, from 4 to 6, from 4 to 8, from 4 to 10, from 5 to 6, from 5 to 7, from 5 to 8, from 5 to 10, from 6 to 8, from 6 to 10, from 6 to 12, from 8 to 10, from 8 to 12, from 10 to 12, from 10 to 15, from 10 to 20, from 12 to 16, from to 20, 1, 2, 3, 4, 5, 6, 7, 8, 9, 10, 11, 12, 13, 14, 15, 16, 17, 18, 19 or 20). In some embodiments, the breast milk distribution system (1) further includes a plurality of reservoirs (3), wherein each of the plurality of reservoirs (3) is configured to be in fluidic communication with a different outlet (13) of the manifold (6). In some embodiments, the outlet is threaded. In some embodiments, the outlet includes internal threads and/or external threads. In some embodiments, the outlet includes a Luer lock connection, wherein the Luer lock connection may releasably connect the outlet and a fluid conduit (5). The outlet may include an O-ring or other gasket to seal to an inlet of a reservoir.

In some embodiments, one inlet branches into from 2 to 20 outlets (e.g., from 2 to 3, from 2 to 4, from 2 to 5, from 2 to 6, from 2 to 7, from 2 to 8, from 3 to 4, from 3 to 5, from 3 to 6, from 3 to 7, from 3 to 8, from 4 to 5, from 4 to 6, from 4 to 8, from 4 to 10, from 5 to 6, from 5 to 7, from 5 to 8, from 5 to 10, from 6 to 8, from 6 to 10, from 6 to 12, from 8 to 10, from 8 to 12, from 10 to 12, from 10 to 15, from 10 to from 12 to 16, or from 15 to 20, or 2, 3, 4, 5, 6, 7, 8, 9, 10, 11, 12, 13, 14, 15, 16, 17, 18, 19 or 20).

In some embodiments, the manifold includes at least one valve. In some embodiments, at least one inlet includes a valve. In some embodiments, at least one outlet includes a valve. In some embodiments, each outlet includes a valve. In some embodiments, the valve includes a ball valve, a batch dispensing valve, a butterfly valve, a diaphragm valve, a diverting valve, a gate valve, a pinch valve, a piston valve, a plug valve, a saddle valve, a solenoid valve, a stem valve, or a stop cock valve. In some embodiments, the valve includes at least one inlet and at least one outlet.

In some embodiments, the outlet of the valve is configured to move between a plurality of the outlets of the manifold. In some embodiments, the valve is a ball valve. In some embodiments, the ball of the ball valve includes at least one inlet and at least one outlet. In some embodiments, the ball may rotate to provide fluidic communication between outlet of the ball and a first outlet of the manifold and/or a second outlet of the manifold.

In some embodiments, the valve includes a solenoid valve. In some embodiments, each outlet of the manifold includes a solenoid valve. The breast milk distribution system (1) can include a drive unit configured to open and close the solenoid valve. In some embodiments, the solenoid valve includes a drive unit configured to open and close the solenoid valve. In some embodiments, the solenoid valve is a pinch valve.

In some embodiments, the breast milk distribution system (1) includes a drive unit (11) configured to open and close the valve (24). In some embodiments, the drive unit (11) is a stepper motor or a linear actuator. In some embodiments, the linear actuator is an electric linear actuator, a hydraulic linear actuator, or a pneumatic linear actuator. In some embodiments, the stepper motor is attached to the manifold, wherein the stepper motor is configured to rotate the manifold (6).

The manifold (6) can be a rotary manifold, in which a plurality of outlets (13) is oriented circumferentially so as to line up with a plurality of reservoirs (3), wherein the manifold is configured to rotate and provide fluidic communication between the inlet (8) and each outlet (13) in sequence.

In some embodiments, the manifold (6) includes a movable, e.g., rotating, member and a stationary member. Each of the movable, e.g., rotating, member and stationary member can include a first end, a second end, and a body disposed therebetween. In some embodiments, each of the movable, e.g., rotating, member and stationary member include a first surface at the first end, and second surface at the second end. In some embodiments, the movable, e.g., rotating, member and/or the stationary member may include a channel disposed therein to transport milk and/or air. The body of each of the movable, e.g., rotating, member and/or the stationary member can have an outer surface.

In some embodiments, the movable, e.g., rotating, member is disposed within the stationary member. Alternatively, in some embodiments, the movable, e.g., rotating, member is disposed outside the stationary member.

In some embodiments, the movable, e.g., rotating, member and/or the stationary member includes an inlet (8) to the manifold (6). In some embodiments, the inlet (8) of the manifold is disposed on the first surface, second surface, or outer surface of the movable, e.g., rotating, member and/or the stationary member. In some embodiments, the movable, e.g., rotating, member and/or the stationary member includes at least one outlet (13) of the manifold (6). In some embodiments, at least one outlet (13) of the manifold is disposed on the first surface, second surface, or outer surface of the movable, e.g., rotating, member and/or the stationary member. In some embodiments, the outlets (13) of the manifold are axially or concentrically disposed in the outer surface of the movable, e.g., rotating, member or the stationary member. In some embodiments, the inlet (8) of the manifold (6) includes a longitudinal axis orthogonally arranged to a longitudinal axis of at least one of the outlets (13) of the manifold (6). In some embodiments, the inlet of the manifold (6) includes a longitudinal axis orthogonally arranged to a longitudinal axis of each of the outlets (13) of the manifold (6).

In some embodiments, the movable, e.g., rotating, member and/or the stationary member include a fluid conduit (5) disposed therein, e.g., within the body. In some embodiments, the fluid conduit (5) is disposed in the body of the movable, e.g., rotating, member and/or the stationary member to provide fluidic communication between an inlet (8) of the manifold (6) and an outlet (13) of the manifold (6). In some embodiments, the fluid conduit (5) includes an outlet, and wherein the diameter of the outlet of the fluid conduit (5) includes the same diameter as the outlets (13) of the manifold (6). In alternative embodiments, the diameter of the outlet of the fluid conduit (5) is larger than the diameter of the outlets (13) of the manifold (6). In still other embodiments, the diameter of the outlet of the fluid conduit (5) is smaller than the diameter of the outlets (13) of the manifold (6). In some embodiments, the movable, e.g., rotating, member is configured to rotate and provide fluidic communication between the outlet of the fluid conduit (5) and the outlet (13) of the manifold (6), thus providing fluidic communication between the inlet (8) of the manifold and that outlet (13) of the manifold (6). In such an embodiment, the inlet (8) of the manifold (6) may or may not be in fluidic communication with other outlets (13) of the manifold.

In some embodiments, the manifold (6) includes (i) a movable, e.g., rotating, member including the inlet (8) of the manifold (6) and a fluid conduit, wherein the inlet (8) of the manifold (6) and the fluid conduit are in fluidic communication, and (ii) a stationary member including the plurality of outlets of the manifold (6); wherein the movable, e.g., rotating, member is configured to move, e.g., rotate, and align the fluid conduit (5) with each of the plurality of outlets (13) of the manifold (6). In some embodiments, the movable, e.g., rotating, member is axially or concentrically arranged within the stationary member. In some embodiments, the outlets of the manifold (6) are radially disposed in the stationary member.

In some embodiments, the breast milk distribution system (1) includes a breast cup (2) configured to receive a nipple; and a manifold (6) in fluidic communication with the breast cup (2), wherein the manifold (6) includes an inlet (8) and an outlet (13) configured to move from a first position to a second position. In some embodiments, each of the plurality of reservoirs (3) are configured to be in fluidic communication with the outlet of the manifold. In some embodiments, the outlet (13) of the manifold (6) is configured to be in fluidic communication with one reservoir at a time. In some embodiments, the milk distribution system (1) further includes a drive unit (11) configured to move the outlet (13). In some embodiments, the drive unit (11) is a stepper motor or a linear actuator. In some embodiments, the linear actuator is an electric linear actuator, a hydraulic linear actuator, or a pneumatic linear actuator. In some embodiments, the manifold (6) includes the stepper motor, and wherein the stepper motor is configured to radially move the outlet of the manifold (6).

In some embodiments, the manifold (6) includes an arm having the outlet (13) of the manifold, wherein the arm is configured to rotate and provide fluidic communication between the outlet (13) and each reservoir (3) individually. Thus, in some embodiments, the breast milk distribution system (1) further includes an arm, wherein the fluid conduit is disposed in and/or on the arm. In some embodiments, the arm includes an articulating arm. In some embodiments, the arm is hollow, and the fluid conduit (5) is disposed inside the arm. In some embodiments, the fluid conduit (5) is releasably connected to the arm.

Figure 5A:
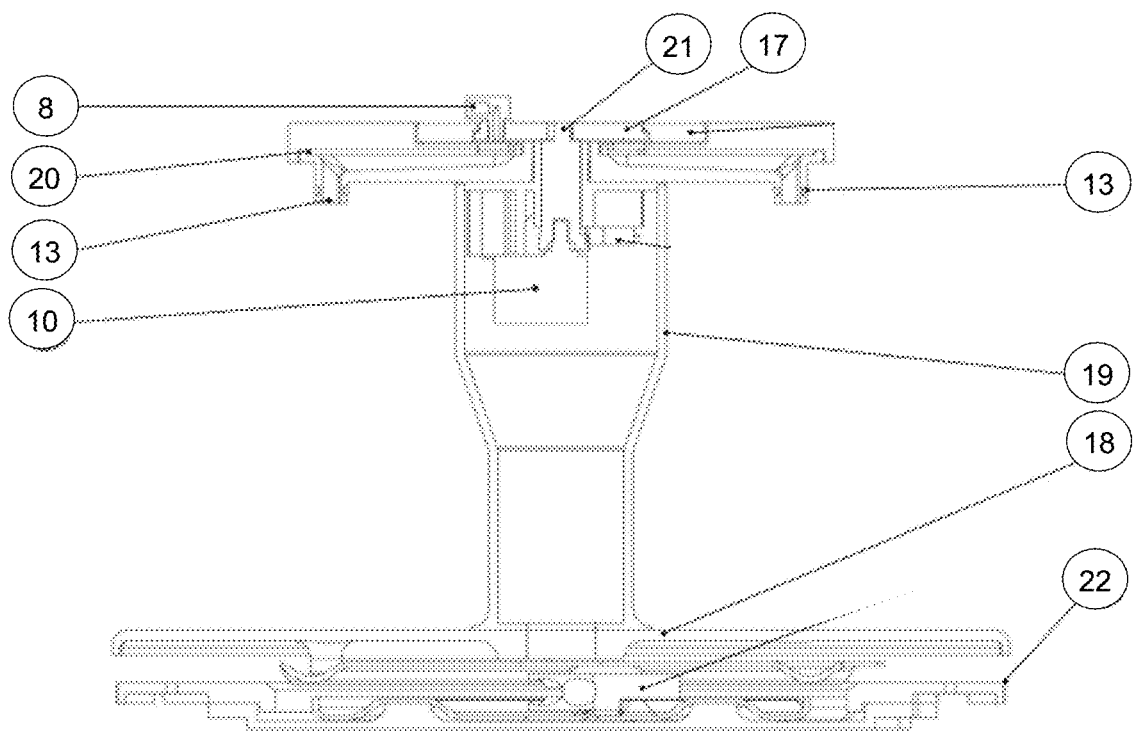
FIGS. 5A-5B show a breast milk distribution system including a manifold with four arms, an inlet (8), outlet (13), alignment plate (17), weighing plate (18), vertical body (19), gasket (20), drive dog (21), stationary base (22), and stepper motor (10).
Figure 5B:
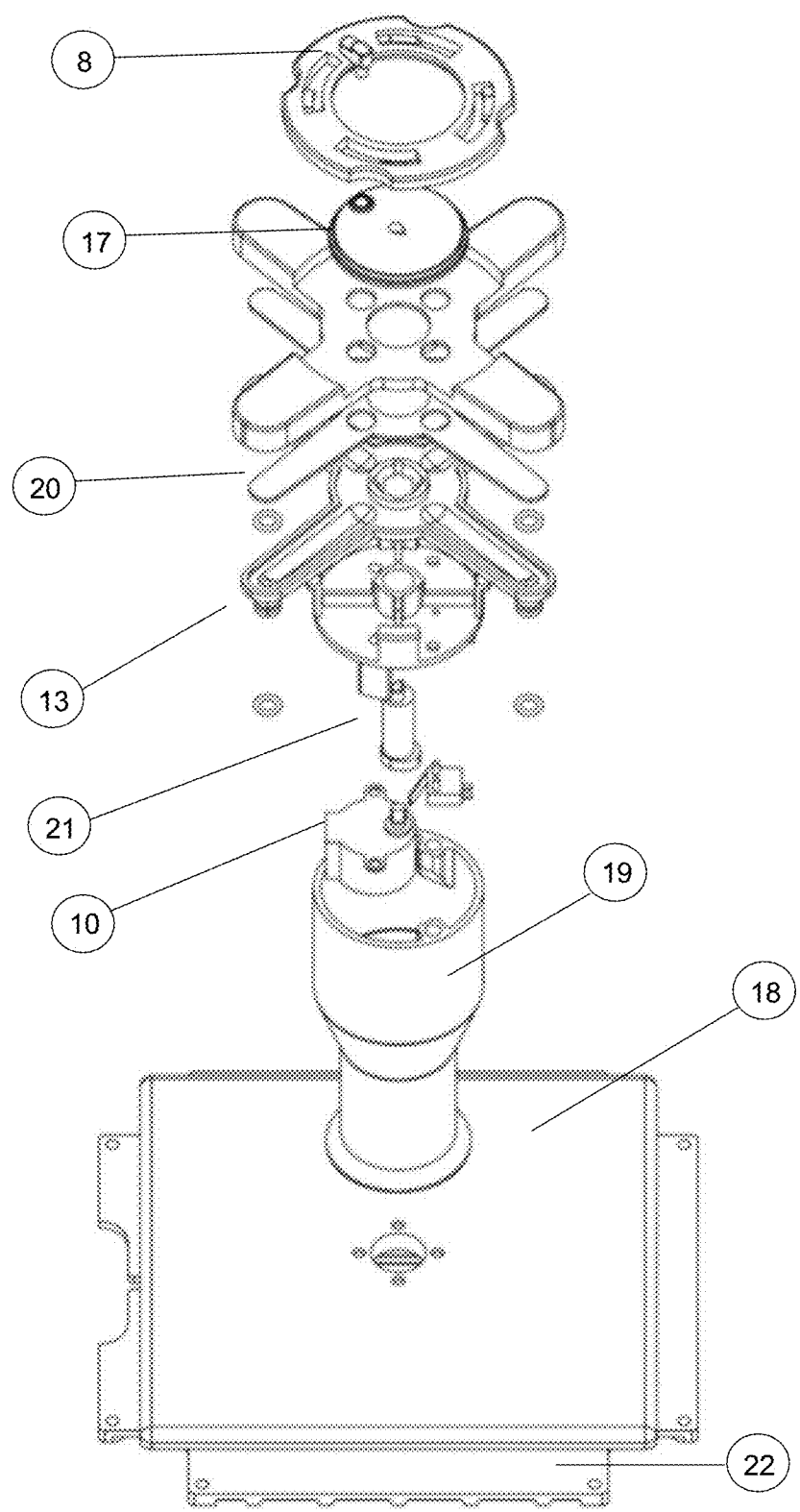

In some embodiments, the manifold (6) includes a stationary portion with two or more arms, e.g., four, as shown in FIGS. 5A and 5B. Each arm has a channel connecting an inlet (8) and an outlet (13), which is configured to be in fluidic communication with a reservoir. For example, the outlets may have an or other seal to seal to the reservoirs. The arms may include a top plate and a bottom plate that are sealed with a gasket (20). The manifold may also include an alignment plate (17) that has an inlet (8). The alignment plate can be moved, e.g., rotated, to align its inlet with that of one of the arms of the manifold. The alignment plate inlet is in fluidic communication with a fluidic conduit from a breast cup. The manifold may include a motor (10), e.g., a stepper motor, with an associated drive dog (21) to mate with the alignment plate, and a vertical body (19) to move the alignment plate and support the arms.

Reservoir Enclosure

The breast milk distribution system may include a reservoir enclosure (4). The reservoir (3) may be within a reservoir enclosure (4). In some embodiments, a plurality of reservoirs (3) is disposed in an enclosure (4). The manifold may be within the enclosure.

The enclosure (4) is advantageous in that milk may be stored for a prolonged period of time, e.g., at least 10 minutes, at least 15 minutes, at least 20 minutes, at least 30 minutes, at least 40 minutes, at least 45 minutes, at least 60 minutes, at least 1.5 hours, at least 2 hours, at least 3 hours, at least 4 hours, at least 5 hours, at least 6 hours, at least 7 hours, at least 8 hours, at least 9 hours, or at least 10 hours.

The enclosure (4) may allow the milk to safely cool for prolonged storage. In some embodiments, the enclosure (4) may maintain the milk below about 6° C. (e.g., about 5° C., about 5.5° C., about 4.5° C., about 4° C., about 3.5° C., about 3° C., about 2.5° C., about 2° C., about 1.5° C., about 1° C., about 0.5° C., or about 0° C.) for a prolonged period of time (e.g., at least 10 minutes, at least 15 minutes, at least 20 minutes, at least 30 minutes, at least 40 minutes, at least 45 minutes, at least 60 minutes, at least 1.5 hours, at least 2 hours, at least 3 hours, at least 4 hours, at least 5 hours, at least 6 hours, at least 7 hours, at least 8 hours, at least 9 hours, or at least 10 hours).

In some embodiments, the enclosure (4) includes a cooling element. The cooling element may be an ice pack and may also include insulation or heat resistant material. In some embodiments, the enclosure (4) includes a plurality of ice packs, such as from 2 to 20 (e.g., 2 to 3, 2 to 4, 2 to 5, 2 to 6, 2 to 7, 2 to 8, 2 to 9, 2 to 10, 2 to 11, 2 to 12, 3 to 4, 3 to 5, 3 to 6, 2 to 8, 3 to 10, 4 to 5, from 4 to 6, 4 to 8, 4 to 10, 4 to 12, 5 to 10, 6 to 8, 6 to 10, 6 to 12, 8 to 10, 8 to 12, 10 to 12, 10 to 20, 1, 2, 3, 4, 5, 6, 7, 8, 9, 11, 12, 13, 14, 15, 16, 17, 18, 19, or 20). The ice pack may be stored in a freezer and then placed in the enclosure before the initiation of breast pumping.

In some embodiments, the cooling element substantially surrounds the reservoir (3). In some embodiments, the cooling element, e.g., the ice pack, is in contact with at least about 5% of the reservoir (3) (e.g., about 10%, about 20%, about 25%, about 30%, about 35%, about 40%, about 45%, about 50%, about 60%, about 70%, about 75%, about 80%, about 90%, or about 95%). In some embodiments, the cooling element conforms to the reservoir (3). In some embodiments, the cooling element is a deformable ice pack.

In some embodiments, the enclosure (4) includes an internal recess, in which the reservoir (3) is configured to be placed in the recess. In some embodiments, following placement in the recess, the outer surface of the reservoir (3) is in contact with an internal surface of the recess. In some embodiments, at least about 5% (e.g., about 10%, about 20%, about 25%, about 30%, about 35%, about 40%, about 45%, about 50%, about 60%, about 70%, about 75%, about 80%, about 90%, or about 95%) of the outer surface of the reservoir (3) is in contact with the inner surface of the recess.

In some embodiments, the enclosure (4) includes a releasably attached tray, in which the tray includes a plurality of recesses (e.g., 2 to 3, 2 to 4, 2 to 5, 2 to 6, 2 to 7, 2 to 8, 2 to 9, 2 to 10, 2 to 11, 2 to 12, 3 to 4, 3 to 5, 3 to 6, 2 to 8, 3 to 10, 4 to 5, from 4 to 6, 4 to 8, 4 to 10, 4 to 12, 5 to 10, 6 to 8, 6 to 10, 6 to 12, 8 to 10, 8 to 12, 10 to 12, 10 to 20, 1, 2, 3, 4, 5, 6, 7, 8, 9, 10, 11, 12, 13, 14, 15, 16, 17, 18, 19, or 20). In some embodiments, the tray includes the cooling element. In some embodiments, the tray includes an ice pack. In some embodiments, the tray is substantially formed from an ice pack.

In some embodiments, the reservoir (3) includes a recess. In some embodiments, the cooling element, e.g., the ice pack, is configured to be placed in the recess. In some embodiments, at least about 5% (e.g., about 10%, about 20%, about 25%, about 30%, about 35%, about 40%, about 45%, about 50%, about 60%, about 70%, about 75%, about 80%, about 90%, or about 95%) of the outer surface of the cooling element is in contact with the inner surface of the recess.

In some embodiments, the enclosure (4) is a cooler. In some embodiments, the enclosure (4) is electrically connected to a power source (12). In some embodiments, the enclosure (4) includes a refrigerant, e.g., a thermoelectric cooler. The reservoir may also include a thermostat to regulate the temperature.

In some embodiments, the enclosure includes a load cell or weight sensor, e.g., a scale. In some embodiments, the weight sensor may be disposed underneath the reservoir (3), such that the weight of the reservoir (3) is measured. In some embodiments, the weight sensor is disposed in a weighing plate (18). In some embodiments, the weight of the reservoir (3) is measured over time using the weight sensor or load cell. In some embodiments, the weight of the reservoir (3) over time may be used to calculate flow rate of milk during a pumping session. In some embodiments, the weight of the reservoir (3) may be used to determine the volume of milk in the reservoir (3), the identity of reservoirs (3) filled or empty, or when a pumping cycle is complete.

In some embodiments, the enclosure further includes a pressure source.

In some embodiments, the enclosure (4) includes a lid (23). Various elements described herein may be disposed in the lid (23) of the enclosure (4), including a pressure source, a drive unit (11), and the manifold (6).

In some embodiments, closure of the lid (23) is configured to provide fluidic communication between at least one reservoir and at least one outlet of the manifold. For example, when the lid (23) of the enclosure (4) is open, the reservoirs (3) may not be in fluidic communication with the manifold (6), but upon closure of the lid (23) of the enclosure (4), at least one of the reservoirs (3) may then be placed in fluidic communication with the manifold (6).

Furthermore, the enclosure (4) may also include a pillow, such that the user may use the enclosure (4) as a pillow while resting or sleeping. In some embodiments, the reservoir (3) and/or enclosure (4) includes padding, cushioning, or stuffing. In some embodiments, the enclosure (4) includes a shape which encourages stillness during rest and/or sleep, e.g., head and/or neck support.

Alternatively, the reservoir (3) or enclosure (4) may be wearable, such as including at least one fastener, e.g., a clip and/or strap, to secure the reservoir (3) or enclosure (4) to the user, e.g., the waist of a user. While the present system is advantageous in that it may be used to breast pump while resting or sleeping, the system may also be used while going about daily activities, such as working, caring for an infant, etc.

Drive Unit and Control Unit

The breast milk distribution system (1) may include a drive unit (11). The drive unit (11) provides power to the elements of the breast milk distribution system (1).

In some embodiments, the drive unit (11) is a stepper motor or a linear actuator. In some embodiments, the linear actuator is an electric linear actuator, a hydraulic linear actuator, or a pneumatic linear actuator. In some embodiments, the drive unit is a stepper motor.

The drive unit (11) may be electrically connected to the manifold, pressure source (e.g., the negative pressure source (9) or the positive pressure source), or the control valve (10).

The breast milk distribution system can include a drive unit (11), e.g., one configured to move at least one reservoir (3) or the manifold (6). In some embodiments, the stepper motor is attached to the manifold (6), and the stepper motor is configured to move the manifold (6), e.g., the movable, e.g., rotating, member of the manifold (6).

In some embodiments, the breast milk distribution system (1) may include a control unit. The drive unit (11) may include a control unit. The control unit provides instructions to the drive unit (11), e.g., pre-programmed instructions or instructions provided by an external computer. The pre-programmed instructions or instructions provided by an external computer may be pumping instructions, heating instructions, cooling instructions, manifold instructions, time instructions, etc. For example, the control unit can be configured to (i) send a signal to the valve (24) to open and close or (ii) send a signal to the drive unit (11) to move, e.g., rotate, the movable, e.g., rotating, member.

Fluid Conduit

The breast milk distribution system may include at least one fluid conduit (5) to provide movement of milk and other fluids, e.g., air.

The fluid conduits (5) may include tubing. The fluid conduit (5) may include a food contact substance. The fluid conduit (5) may include an infant grade material. The fluid conduit (5) may include polyacetal, polyoxymethylene (POM), chlorinated polyvinyl chloride (CPVC), ethylene tetrafluoroethylene (ETFE), ethylene-vinyl acetate (EVA), fluorinated ethylene propylene (FEP), nylon, polyether ether ketone (PEEK), perfluoroalkoxy alkane (PFA), PC, polyethylene, PP, PTFE (e.g., Teflon), PVC, PVDF, thermoplastic elastomer (TPE), fluorosilicone, gum, latex, neoprene, polyurethane, rubber, rubber particles encapsulated in a PP matrix (e.g., Santoprene), or silicon. In some embodiments, the breast milk distribution system (1) includes an infant grade material.

In some embodiments, the fluid conduit (5) includes an internal diameter (ID) from about 0.5 mm to about 50 mm (e.g., about 0.5 mm to about 1 mm, about 0.5 mm to about 1.5 mm, about 0.5 mm to about 2 mm, about 0.5 mm to about 2.5 mm, about 0.5 mm to about 3 mm, about 0.5 mm to about 3.5 mm, about 0.5 mm to about 4 mm, about 0.5 mm to about 4.5 mm, about 0.5 mm to about 5 mm, about 0.5 mm to about 5.5 mm, about 0.5 mm to about 6 mm, about 0.5 mm to about 6.5 mm, about 0.5 mm to about 7 mm, about 0.5 mm to about 7.5 mm, about 0.5 mm to about 10 mm, about 1 mm to about 1.5 mm, about 1 mm to about 2 mm, about 1 mm to about 2.5 mm, about 1 mm to about 3 mm, about 1 mm to about 3.5 mm, about 1 mm to about 4 mm, about 1 mm to about 4.5 mm, about 1 mm to about 5 mm, about 1 mm to about 10 mm, about 1 mm to about 25 mm, about 1 mm to about 30 mm, about 1 mm to about 40 mm, about 2 mm to about 2.5 mm, about 2 mm to about 3 mm, about 2 mm to about 3.5 mm, about 2 mm to about 4 mm, about 2 mm to about 4.5 mm, about 2 mm to about 5 mm, about 3 mm to about 4 mm, about 3 mm to about 5 mm, about 4 mm to about 5 mm, about 4 mm to about 6 mm, about 5 mm to about 8 mm, about 5 mm to about 10 mm, about 5 mm to about 15 mm, about 5 mm to about 25 mm, about 5 mm to about 50 mm, about 10 mm to about 25 mm, about 20 mm to about 30 mm, about 25 mm to about 50 mm, about 30 mm to about 40 mm, about 30 mm to about 50 mm, or about 40 mm to about 50 mm).

In some embodiments, the fluid conduit (5) includes an outer diameter (OD) from about 0.5 mm to about 50 mm (e.g., about 0.5 mm to about 1 mm, about 0.5 mm to about 1.5 mm, about 0.5 mm to about 2 mm, about 0.5 mm to about 2.5 mm, about 0.5 mm to about 3 mm, about 0.5 mm to about 3.5 mm, about 0.5 mm to about 4 mm, about 0.5 mm to about 4.5 mm, about 0.5 mm to about 5 mm, about 0.5 mm to about 5.5 mm, about 0.5 mm to about 6 mm, about 0.5 mm to about 6.5 mm, about 0.5 mm to about 7 mm, about 0.5 mm to about 7.5 mm, about 0.5 mm to about 10 mm, about 1 mm to about 1.5 mm, about 1 mm to about 2 mm, about 1 mm to about 2.5 mm, about 1 mm to about 3 mm, about 1 mm to about 3.5 mm, about 1 mm to about 4 mm, about 1 mm to about 4.5 mm, about 1 mm to about 5 mm, about 1 mm to about 10 mm, about 1 mm to about 25 mm, about 1 mm to about 30 mm, about 1 mm to about 40 mm, about 2 mm to about 2.5 mm, about 2 mm to about 3 mm, about 2 mm to about 3.5 mm, about 2 mm to about 4 mm, about 2 mm to about 4.5 mm, about 2 mm to about 5 mm, about 3 mm to about 4 mm, about 3 mm to about 5 mm, about 4 mm to about 5 mm, about 4 mm to about 6 mm, about 5 mm to about 8 mm, about 5 mm to about 10 mm, about 5 mm to about 15 mm, about 5 mm to about 25 mm, about 5 mm to about 50 mm, about 10 mm to about 25 mm, about 20 mm to about 30 mm, about 25 mm to about 50 mm, about 30 mm to about 40 mm, about 30 mm to about 50 mm, or about 40 mm to about 50 mm).

The fluid conduit (5) may be selected to have a desired durometer to provide the preferred amount of flexibility for allowance of movement. For example, the fluid conduit (5) may have a durometer from about 25 Shore A scale and about 100 Shore D scale, including 25 A, 30 A, 35 A, 40 A, 45 A, 50 A, 55 A, 65 A, 70 A, 75 A, 80 A, 85 A, 90 A, 95 A, 100 A, 10 D, 25 D, 30 D, 35 D, 40 D, 45 D, 50 D, 55 D, 60 D, 65 D, 75 D, 80 D, 85 D, 90 D, 95 D, 100 D, or any durometer therebetween.

The fluid conduit (5) may be configured for ease of cleaning. For example, the breast milk distribution system may be run through with water to clean the fluid conduit (5).

The breast milk distribution system (1) may include any number of fluid conduits (5), e.g., one, two, three, four, five, six, seven, eight, nine, ten, etc. A portion of fluid conduits (5) may provide air flow to the breast milk distribution system (1), while other fluid conduits (5) transport milk.

In some embodiments, the breast milk distribution system (1) includes a first fluid conduit (5) providing fluidic communication between the breast cup (2) and the manifold (6).

Additional fluid conduits (5) may transport milk from a second breast. In some embodiments, a first breast cup (2) is connected to a first fluid conduit (5), and a second breast cup (2) is connected to a second fluid conduit (5). In some embodiments, the first fluid conduit (5) and the second fluid conduit (5) merge into a third fluid conduit (5). In some embodiments, the third fluid conduit (5) connects to the manifold (6).

In some embodiments, additional fluid conduits (5) may transport milk to additional reservoirs (3). In some embodiments, the milk from different breast pumping sessions is transported to the first reservoir (3) and/or second reservoir (3) through a fluid conduit (5). The milk transported to the first reservoir (3) and/or second reservoir (3) may be transported with the same or different fluid conduit (5), e.g., a first fluid conduit (5) and a second fluid conduit (5).

In some embodiments, the milk distribution system (1) includes a fluid conduit (5) providing fluidic communication between the breast cup (2) and the inlet (8) of the manifold (6). In some embodiments, the breast milk distribution system (1) further includes a fluid conduit (5) providing fluidic communication between the inlet of the manifold (8) and the outlet of the manifold (13). In some embodiments, the breast milk distribution system further includes a plurality of fluid conduits (5) providing fluidic communication between each of the outlets (13) of the manifold (6) and the plurality of reservoirs (3).

A fluid conduit may have any appropriate connector at each end for connection to the breast cup (2) and breast milk distribution system (1). Examples of connectors include Luer connectors, threaded connectors, and slip fit connectors.

Valves

The breast milk distribution system (1) may include one or more valves. In some embodiments, the valve is a control valve, an open-close valve, a one directional valve, a relief valve, a quick-release valve, an inflation valve, or a slow-leak valve. In some embodiments, the valve is a mechanical valve, an inflation valve, an umbrella valve, a butterfly valve, a disk valve, a non-drip valve, a duckbill valve, a ball valve, a batch dispensing valve, a diaphragm valve, a gate valve, a diverting valve, a pinch valve, a piston valve, a plug valve, a saddle valve, a solenoid valve, a stem valve, a stop cock valve, or a three-way valve.

Figure 3:
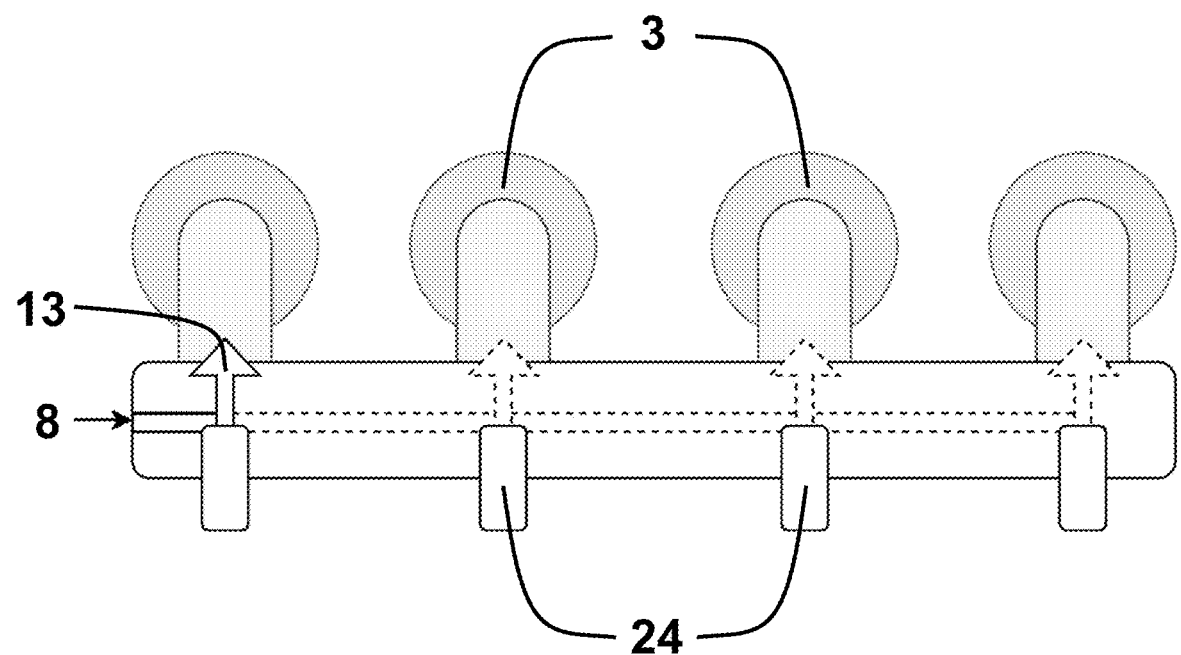
FIG. 3 shows a schematic drawing of a breast milk distribution system (1) including (i) a plurality of reservoirs (3) and (ii) a manifold (6) having an inlet (8) and at least out outlet (13), wherein each of the reservoirs (3) includes a valve (24), in particular, a solenoid valve, wherein the solenoid valve is configured to provide fluidic communication between an outlet of the manifold (13) and a reservoir (3).

The breast milk distribution system (1) can include a valve (24). Such a valve (24) is advantageous in that it can provide selective fluidic communication to a plurality of reservoirs (3), as shown in FIG. 3. Thus, in some embodiments, the breast milk distribution system (1), can include a manifold (6) in fluidic communication with a breast cup (2), wherein the manifold (6) includes an inlet (8) and a plurality of outlets (13); and a valve (24) in fluidic communication with the manifold (6). In some embodiments, the breast milk distribution system (1) includes a plurality of valves (24), wherein each outlet (13) of the manifold (6) or the inlet of each reservoir (3) can include a valve (24). In some embodiments, the breast milk distribution system (1) is configured to close a valve (24) to a reservoir following a breast pumping session in which that reservoir (3) was filled.

The breast milk distribution system (1) may include a control valve (10). The control valve (10) may be in fluidic communication with the breast cup (2) and the negative pressure source (9). In some embodiments, the fluid conduit (5) providing fluidic communication between the breast cup (2) and negative pressure source (9) includes the control valve (10). The control valve (10) may provide positive pressure to the breast cup (2) and/or the negative pressure source (9) in order to decrease the negative pressure provided by the negative pressure source (9), and reduce or stop milk flow, e.g., by depressurizing the nipple.

The positive pressure provided by the control valve (10) may be between 0 mmHg to 400 mmHg, e.g., about 25 mmHg. In some embodiments, the positive pressure is 0 mmHg, e.g., open atmospheric pressure. In some embodiments, the negative pressure source (9) and control valve (10) are contained within the same feature.

In some embodiments, the breast milk distribution system may include an open-close valve. In some embodiments, the control valve includes an open-close valve. The open-close valve may be configured to open and close fluidic communication between a first element and a second element. In some embodiments, the first element can include a reservoir (3), fluid conduit (5), a breast cup (2), a manifold (6), or the ambient atmosphere. In some embodiments, the second element can include a reservoir (3), fluid conduit (5), a breast cup (2), a manifold (6), or the ambient atmosphere.

The breast milk distribution system (1) may include one or more one directional valves (15) or anti-backflow valves, e.g., a plurality of one directional valves (15).

The one directional valve (15) may be a duckbill valve or other type of one directional valve.

In some embodiment, the one directional valve (15) may be placed in a fluid conduit (5), e.g., to prevent backflow of milk. In some embodiments, the one directional valve (15) is configured to allow fluid flow from the breast cup (2) to the manifold (6). In some embodiments, the one directional valve (15) is disposed in the first fluid conduit (5). In some embodiments, the one directional valve (15) may prevent air from entering the first fluid conduit (5), thereby maintaining negative pressure to move the milk.

In some embodiments, the one directional valve (15) is between the breast cup (2) and the reservoir (3), such that milk cannot backflow from the reservoir (3).

Sensors

The breast milk distribution system may also include at least one sensor. Sensors include weight sensors, load cells, temperature sensors, pressure sensors, pH sensors, flow sensors, viscosity sensors, volume sensors, etc. Sensors may be in at least one fluid conduit (5), in the pump system, in the reservoir (3), or in the reservoir enclosure (4).

In some embodiments, the breast milk distribution system includes at least one weight sensor or load cell. In some embodiments, the weight sensor is disposed in the bottom of the reservoir (3). In some embodiments, the weight sensor is disposed in the bottom of the reservoir enclosure (4), underneath a plurality of reservoirs (3), e.g., a weighing plate (18), such that the weight of the reservoirs may be measured. Weight sensors may track the weight of the reservoirs (3) over time. In some embodiments, weight data may be used to determine flow rate of milk during a pumping session. In some embodiments, weight sensors may be used to determine the volume of milk inside of a reservoir (3).

In some embodiments, the breast milk distribution system includes at least one temperature sensor, e.g., a thermocouple. In some embodiments, the breast pump includes a plurality of temperature sensors. Temperature sensors may provide time history data. Using the circadian baseline, deviations from baseline may be identified. In some embodiments, the reservoir (3) includes a temperature sensor. A change in temperature of milk may indicate spoiled milk.

The breast milk distribution system may include at least one pressure sensor. In some embodiments, the reservoir (3) includes a pressure sensor. In some embodiments, each reservoir (3) includes a pressure sensor. A pressure sensor in a reservoir can be advantageous in determining over pressurization of the reservoir (3), e.g., as a result of milk being pumped into the reservoir (3).

The breast milk distribution system may include at least one pH sensor. In some embodiments, the breast milk distribution system includes a plurality of pH sensors. In some embodiments, the pH sensor is an ion sensitive glass electrode.

The breast milk distribution system may include at least one flow sensor. In some embodiments, the breast pump includes a plurality of flow sensors. In some embodiments, a fluid conduit (5) includes a flow sensor. A flow sensor may detect the rate of fluid flow in the fluid conduit (5).

The breast milk distribution system may include at least one volume sensor. In some embodiments, the breast milk distribution system includes a plurality of volume sensors. In some embodiments, the reservoir (3) includes a volume sensor. A volume sensor may detect the level of milk in the reservoir (3).

The breast milk distribution system may include at least one optical sensor. In some embodiments, the breast pump includes a plurality of optical sensors. The optical sensor may include a light source, e.g., an LED light source, and associated photodetector. The light source in one example emits light at different wavelengths within the visible spectrum, including a violet light, a blue light, a green light, a yellow light, an orange light and a red light. In various embodiments, the optical sensor includes a singular light source or a plurality of light sources, similarly the photodetector may include a single photodetector or a plurality of photodetectors. In some embodiments, the reservoir (3) may include an optical sensor.

In some embodiments, the optical sensor may sense the clarity of the milk in the reservoir (3). The clarity of the milk may be indicative of fat content, e.g., a lower clarity may be indicative of a higher fat content.

The breast milk distribution system may include at least one viscometer. In some embodiments, the breast milk distribution system includes a plurality of viscometers. In some embodiments, the reservoir (3) includes a viscometer. The viscometer may sense the viscosity of the milk, e.g., the milk in the reservoir (3).

In some embodiments, the breast milk distribution system (1) includes a Hall effect sensor. A Hall effect sensor is a sensor which detects the presence and magnitude of a magnetic field using the Hall effect. A Hall effect sensor is advantageous in that it may allow the breast milk distribution system to collect information on whether the system completes actions. The information collected by the Hall effect sensor may be used to provide assurance and aid in diagnosing any errors.

Pressure Source

The breast milk distribution system (1) can include a pressure source, e.g., a negative pressure source (9) and/or a positive pressure source. Specifically, the pressure source is configured to be used to move fluids, such as air, water, milk, and/or cleaning fluid, in the milk distribution system (1). In some embodiments, the breast milk distribution system (1) includes a plurality of pressure sources (e.g., 1, 2, 3, 4, 5, 6, 7, 8, 9 or 10). In some embodiments, at least one pressure source is a peristaltic pump. In some embodiments, at least one pressure source is a vacuum pump, e.g., which is capable of producing negative and positive pressure.

In some embodiments, the breast milk distribution system (1) includes a negative pressure source (9) that provides negative pressure to the breast cup (2), and thus the nipple of the breast in order to express milk. Additionally, the negative pressure source (9) may be configured to transport milk from a breast cup (2) to the manifold (6). In some embodiments, the negative pressure source (9) is a vacuum pump.

In some embodiments, the breast milk distribution system (1) includes a positive pressure source that provides positive pressure to the breast cup (2) to aid in transportation of milk. In some embodiments, the positive pressure source is a pressure pump, a manually compressible chamber, a vacuum pump, a peristaltic pump, or a valve to the ambient atmosphere.

In some embodiments, pressure applied to the breast cup (2) varies. In some embodiments, the pressure source applies pressure to the breast cup (2) in for 1 to 20 cycles (e.g., 1 to 2 cycles, 1 to 3 cycles, 1 to 4 cycles, 1 to 5 cycles, 1 to 6 cycles, 1 to 7 cycles, 1 to 8 cycles, 1 to 9 cycles, 1 to 10 cycles, 1 to 15 cycles, 2 to 3 cycles, 2 to 4 cycles, 2 to 5 cycles, 3 to 7 cycles, 4 to 6 cycles, 5 to 10 cycles, 5 to cycles, 10 to 15 cycles, 15 to 20 cycles, 1 cycle, 2 cycles, 3 cycles, 4 cycles, 5 cycles, 6 cycles, 7 cycles, 8 cycles, 9 cycles, 10 cycles, 11 cycles, 12 cycles, 13 cycles, 14 cycles, 15 cycles, 16 cycles, 17 cycles, 18 cycles, 19 cycles, or 20 cycles). A first cycle may apply a maximum negative pressure of 0 mmHg to about 400 mmHg and/or a maximum positive pressure of about 0 mmHg to about 400 mmHg of positive pressure. A second cycle may apply a maximum negative pressure of about 0 mmHg to about 400 mmHg and/or a maximum positive pressure of about 0 mmHg to about 400 mmHg of positive pressure. Likewise, a third, fourth, fifth, etc., cycle, may apply a maximum negative pressure of about 0 mmHg to about 400 mmHg and/or a maximum positive pressure of about 0 mmHg to about 400 mmHg of positive pressure.

Figure 4:
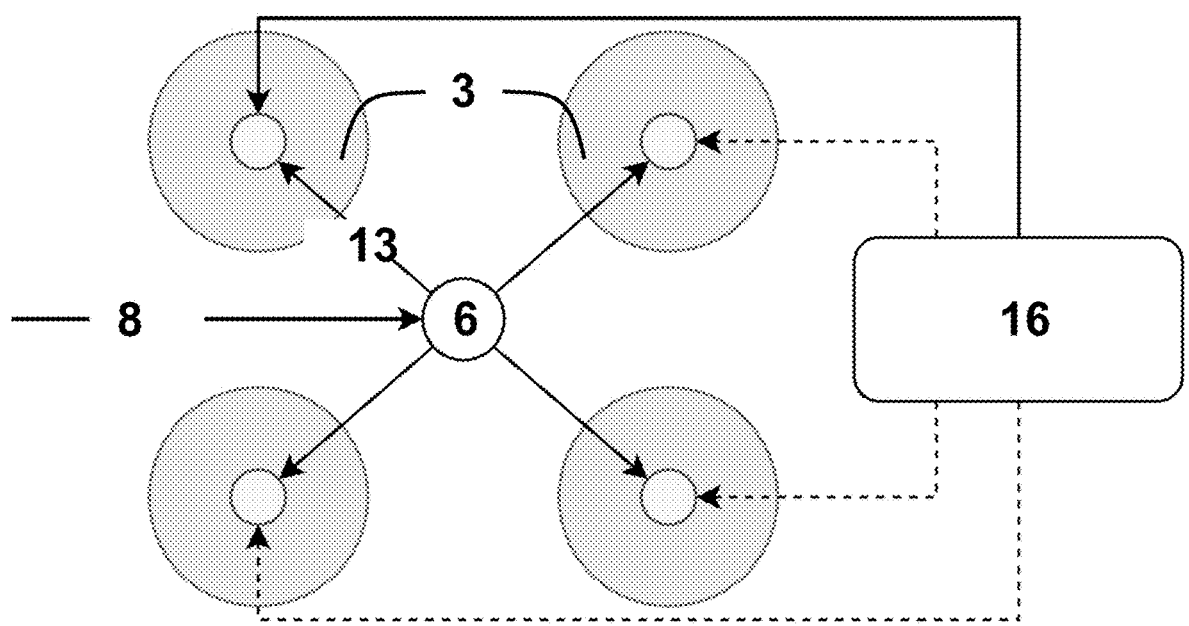
FIG. 4 shows a schematic drawing of a breast milk distribution system (1) including (i) a plurality of reservoirs (3), (ii) a pressure source (16), (iii) and a manifold (6) having an inlet (8) and at least one outlet (13), wherein the pressure source (16) is configured to provide fluidic communication between an outlet of the manifold (13) and a reservoir (3).

In some embodiments, the breast milk distribution system (1) includes a pressure source in fluidic communication with the breast cup (2), the manifold (6), and/or at least one of the plurality of reservoirs (3). In some embodiments, the breast milk distribution system (1) includes a pressure source configured to transport milk from the breast cup (2) to a reservoir (3). In some embodiments, this pressure source is the same pressure source used to pressurize a breast cup. In some embodiments, this pressure source is a different pressure source than is used to pressurize a breast cup. In some embodiments, this pressure source is a peristaltic pump, e.g., connected to a fluid conduit between the breast cup and the manifold. Such a pump can aid in transporting milk to the manifold. In some embodiments, breast milk distribution system (1) includes a fluid conduit (5) in fluidic communication with the breast cup (2), the manifold (6), at least one reservoir (3), and/or another fluid conduit (5) providing fluidic communication between components of the breast milk distribution system (1). In some embodiments, the pressure source is a negative pressure source (9) or a positive pressure source. In some embodiments, the pressure source is configured to open and/close an outlet of the manifold (13). In some embodiments, the pressure source is configured to open and/close an inlet of a reservoir, as shown in FIG. 4. In some embodiments, the inlet of a reservoir (3) is nominally closed and is configured to open upon pressurization provided by a pressure source.

The negative pressure source (9) may provide a negative pressure from about 0 mmHg to about 400 mmHg (e.g., about 0 mmHg to about 10 mmHg, about 0 mmHg to about 20 mmHg, about 0 mmHg to about 30 mmHg, about 0 mmHg to about 40 mmHg, about 0 mmHg to about 50 mmHg, about 0 mmHg to about 60 mmHg, about 0 mmHg to about 70 mmHg, about 0 mmHg to about 80 mmHg, about 0 mmHg to about 90 mmHg, about 0 to about 100 mmHg, about 0 mmHg to about 110 mmHg, about 0 mmHg to about 120 mmHg, about 0 mmHg to about 130 mmHg, about 0 to about 140 mmHg, about 0 mmHg to about 150 mmHg, about 0 to about 175 mmHg, about 0 mmHg to about 200 mmHg, about 0 mmHg to about 225 mmHg, about 0 mmHg to about 250 mmHg, about 0 mmHg to about 275 mmHg, about 0 mmHg to about 300 mmHg, about 0 to about 350 mmHg, about 0 mmHg to about 400 mmHg, about 10 mmHg to about 20 mmHg, about 10 mmHg to about 30 mmHg, about 10 mmHg to about 40 mmHg, about 10 mmHg to about 50 mmHg, about 10 mmHg to about 60 mmHg, about 10 mmHg to about 70 mmHg, about 10 mmHg to about 80 mmHg, about 10 mmHg to about 90 mmHg, about 10 mmHg to about 100 mmHg, about 10 mmHg to about 110 mmHg, about 10 mmHg to about 120 mmHg, about 10 mmHg to about 130 mmHg, about 10 mmHg to about 140 mmHg, about 10 mmHg to about 150 mmHg, about 10 mmHg to about 175 mmHg, about 10 mmHg to about 200 mmHg, about 10 mmHg to about 225 mmHg, about 10 mmHg to about 250 mmHg, about 10 mmHg to about 300 mmHg, about 10 to about 350 mmHg, about 10 mmHg to about 400 mmHg, about 20 mmHg to about 30 mmHg, about 20 mmHg to about 40 mmHg, about 20 mmHg to about 50 mmHg, about 20 mmHg to about 60 mmHg, about 20 mmHg to about 70 mmHg, about 20 mmHg to about 80 mmHg, about 20 mmHg to about 90 mmHg, about 20 mmHg to about 100 mmHg, about 20 mmHg to about 110 mmHg, about 20 mmHg to about 120 mmHg, about 20 mmHg to about 130 mmHg, about 20 mmHg to about 140 mmHg, about 20 mmHg to about 150 mmHg, about 20 mmHg to about 175 mmHg, about 20 mmHg to about 200 mmHg, about 20 mmHg to about 225 mmHg, about 20 mmHg to about 250 mmHg, about 20 mmHg to about 300 mmHg, about 20 to about 350 mmHg, about 20 mmHg to about 400 mmHg, about 25 mmHg to about 50 mmHg, about 25 mmHg to about 75 mmHg, about 25 mmHg to about 100 mmHg, about 30 mmHg to about 40 mmHg, about 30 mmHg to about 50 mmHg, about 30 mmHg to about 60 mmHg, about 30 mmHg to about 70 mmHg, about 30 mmHg to about 80 mmHg, about 30 mmHg to about 90 mmHg, about 30 mmHg to about 100 mmHg, about 30 mmHg to about 110 mmHg, about 30 mmHg to about 120 mmHg, about 30 mmHg to about 130 mmHg, about 30 mmHg to about 140 mmHg, about 30 mmHg to about 150 mmHg, about 30 mmHg to about 175 mmHg, about 30 mmHg to about 200 mmHg, about 30 mmHg to about 225 mmHg, about 30 mmHg to about 250 mmHg, about 30 mmHg to about 300 mmHg, about 30 to about 350 mmHg, about 30 mmHg to about 400 mmHg, about 40 mmHg to about 50 mmHg, about 40 mmHg to about 60 mmHg, about 40 mmHg to about 70 mmHg, about 40 mmHg to about 80 mmHg, about 40 mmHg to about 90 mmHg, about 40 mmHg to about 100 mmHg, about 40 mmHg to about 110 mmHg, about 40 mmHg to about 120 mmHg, about 40 mmHg to about 130 mmHg, about 40 mmHg to about 140 mmHg, about 40 mmHg to about 150 mmHg, about 40 mmHg to about 175 mmHg, about 40 mmHg to about 200 mmHg, about 40 mmHg to about 225 mmHg, about 40 mmHg to about 250 mmHg, about 40 mmHg to about 300 mmHg, about 40 to about 350 mmHg, about 40 mmHg to about 400 mmHg, about 50 mmHg to about 60 mmHg, about 50 mmHg to about 70 mmHg, about 50 mmHg to about 75 mmHg, about 50 mmHg to about 80 mmHg, about 50 mmHg to about 90 mmHg, about 50 mmHg to about 100 mmHg, about 50 mmHg to about 110 mmHg, about 50 mmHg to about 120 mmHg, about 50 mmHg to about 130 mmHg, about mmHg 50 to about 140 mmHg, about 50 mmHg to about 150 mmHg, about 50 mmHg to about 175 mmHg, about 50 mmHg to about 200 mmHg, about 50 mmHg to about 225 mmHg, about 50 mmHg to about 250 mmHg, about 50 mmHg to about 300 mmHg, about 50 to about 350 mmHg, about 50 mmHg to about 400 mmHg, about 60 mmHg to about 70 mmHg, about 60 mmHg to about 80 mmHg, about 60 mmHg to about 90 mmHg, about 60 mmHg to about 100 mmHg, about 60 mmHg to about 110 mmHg, about 60 mmHg to about 120 mmHg, about 60 mmHg to about 130 mmHg, about 60 mmHg to about 140 mmHg, about 60 mmHg to about 150 mmHg, about 60 mmHg to about 175 mmHg, about 60 mmHg to about 200 mmHg, about 60 mmHg to about 225 mmHg, about 60 mmHg to about 250 mmHg, about 60 mmHg to about 300 mmHg, about 60 to about 350 mmHg, about 60 mmHg to about 400 mmHg, about 70 mmHg to about 80 mmHg, about 70 mmHg to about 90 mmHg, about 70 mmHg to about 100 mmHg, about 70 mmHg to about 110 mmHg, about 70 mmHg to about 120 mmHg, about 70 mmHg to about 130 mmHg, about 70 mmHg to about 140 mmHg, about 70 mmHg to about 150 mmHg, about 70 mmHg to about 175 mmHg, about 70 mmHg to about 200 mmHg, about 70 mmHg to about 225 mmHg, about 70 mmHg to about 250 mmHg, about 70 mmHg to about 300 mmHg, about 70 to about 350 mmHg, about 70 mmHg to about 400 mmHg, about 75 mmHg to about 100 mmHg, about 75 mmHg to about 125 mmHg, about 80 mmHg to about 90 mmHg, about 80 mmHg to about 100 mmHg, about 80 mmHg to about 110 mmHg, about 80 mmHg to about 120 mmHg, about 80 mmHg to about 130 mmHg, about 80 mmHg to about 140 mmHg, about 80 mmHg to about 150 mmHg, about 80 mmHg to about 175 mmHg, about 80 mmHg to about 200 mmHg, about 80 mmHg to about 225 mmHg, about 80 mmHg to about 250 mmHg, about 80 mmHg to about 300 mmHg, about 80 to about 350 mmHg, about 80 mmHg to about 400 mmHg, about 90 mmHg to about 100 mmHg, about 90 mmHg to about 110 mmHg, about 90 mmHg to about 120 mmHg, about 90 mmHg to about 130 mmHg, about 90 mmHg to about 140 mmHg, about 90 mmHg to about 150 mmHg, about 90 mmHg to about 175 mmHg, about 90 mmHg to about 200 mmHg, about 90 mmHg to about 225 mmHg, about 90 mmHg to about 250 mmHg, about 90 mmHg to about 300 mmHg, about 90 to about 350 mmHg, about 90 mmHg to about 400 mmHg, about 100 mmHg to about 110 mmHg, about 100 mmHg to about 120 mmHg, about 100 mmHg to about 130 mmHg, about 100 mmHg to about 140 mmHg, about 100 mmHg to about 150 mmHg, about 100 mmHg to about 175 mmHg, about 100 mmHg to about 200 mmHg, about 100 mmHg to about 225 mmHg, about 100 mmHg to about 250 mmHg, about 100 mmHg to about 300 mmHg, about 100 to about 350 mmHg, about 100 mmHg to about 400 mmHg, about 110 mmHg to about 120 mmHg, about 110 mmHg to about 130 mmHg, about 110 mmHg to about 140 mmHg, about 110 mmHg to about 150 mmHg, about 110 mmHg to about 175 mmHg, about 110 mmHg to about 200 mmHg, about 110 mmHg to about 225 mmHg, about 110 mmHg to about 250 mmHg, about 110 mmHg to about 300 mmHg, about 110 to about 350 mmHg, about 110 mmHg to about 400 mmHg, about 120 mmHg to about 130 mmHg, about 120 mmHg to about 140 mmHg, about 120 mmHg to about 150 mmHg, about 120 mmHg to about 175 mmHg, about 120 mmHg to about 200 mmHg, about 120 mmHg to about 225 mmHg, about 120 mmHg to about 250 mmHg, about 120 mmHg to about 300 mmHg, about 120 to about 350 mmHg, about 120 mmHg to about 400 mmHg, about 130 mmHg to about 140 mmHg, about 130 mmHg to about 150 mmHg, about 130 mmHg to about 175 mmHg, about 130 mmHg to about 200 mmHg, about 130 mmHg to about 225 mmHg, about 130 mmHg to about 250 mmHg, about 130 mmHg to about 300 mmHg, about 130 to about 350 mmHg, about 130 mmHg to about 400 mmHg, about 140 mmHg to about 150 mmHg, about 140 mmHg to about 175 mmHg, about 140 mmHg to about 200 mmHg, about 140 mmHg to about 225 mmHg, about 140 mmHg to about 250 mmHg, about 140 mmHg to about 300 mmHg, about 140 to about 350 mmHg, about 140 mmHg to about 400 mmHg, about 150 mmHg to about 175 mmHg, about 150 mmHg to about 200 mmHg, about 150 mmHg to about 225 mmHg, about 150 mmHg to about 250 mmHg, about 150 mmHg to about 300 mmHg, about 150 to about 350 mmHg, about 150 mmHg to about 400 mmHg, about 175 mmHg to about 200 mmHg, about 175 mmHg to about 225 mmHg, about 175 mmHg to about 250 mmHg, about 175 mmHg to about 300 mmHg, about 175 to about 350 mmHg, about 175 mmHg to about 400 mmHg, about 200 mmHg to about 225 mmHg, about 200 mmHg to about 250 mmHg, about 200 mmHg to about 300 mmHg, about 200 to about 350 mmHg, about 200 mmHg to about 400 mmHg, about 225 mmHg to about 250 mmHg, about 225 mmHg to about 300 mmHg, about 225 to about 350 mmHg, about 225 mmHg to about 400 mmHg, about 275 mmHg to about 300 mmHg, about 275 to about 350 mmHg, about 275 mmHg to about 400 mmHg, about 300 mmHg to about 325 mmHg, about 300 to about 350 mmHg, about 300 mmHg to about 400 mmHg, about 325 mmHg to about 350 mmHg, about 325 to about 375 mmHg, about 325 mmHg to about 400 mmHg, about 350 mmHg to about 375 mmHg, about 350 to about 400 mmHg, or about 375 mmHg to about 400 mmHg.

The positive pressure source can provide a positive pressure from about 0 mmHg to about 400 mmHg (e.g., about 0 mmHg to about 10 mmHg, about 0 mmHg to about 20 mmHg, about 0 mmHg to about 30 mmHg, about 0 mmHg to about 40 mmHg, about 0 mmHg to about 50 mmHg, about 0 mmHg to about 60 mmHg, about 0 mmHg to about 70 mmHg, about 0 mmHg to about 80 mmHg, about 0 mmHg to about 90 mmHg, about 0 to about 100 mmHg, about 0 mmHg to about 110 mmHg, about 0 mmHg to about 120 mmHg, about 0 mmHg to about 130 mmHg, about 0 to about 140 mmHg, about 0 mmHg to about 150 mmHg, about 0 to about 175 mmHg, about 0 mmHg to about 200 mmHg, about 0 mmHg to about 225 mmHg, about 0 mmHg to about 250 mmHg, about 0 mmHg to about 275 mmHg, about 0 mmHg to about 300 mmHg, about 0 to about 350 mmHg, about 0 mmHg to about 400 mmHg, about 10 mmHg to about 20 mmHg, about 10 mmHg to about 30 mmHg, about 10 mmHg to about 40 mmHg, about 10 mmHg to about 50 mmHg, about 10 mmHg to about 60 mmHg, about 10 mmHg to about 70 mmHg, about 10 mmHg to about 80 mmHg, about 10 mmHg to about 90 mmHg, about 10 mmHg to about 100 mmHg, about 10 mmHg to about 110 mmHg, about 10 mmHg to about 120 mmHg, about 10 mmHg to about 130 mmHg, about 10 mmHg to about 140 mmHg, about 10 mmHg to about 150 mmHg, about 10 mmHg to about 175 mmHg, about 10 mmHg to about 200 mmHg, about 10 mmHg to about 225 mmHg, about 10 mmHg to about 250 mmHg, about 10 mmHg to about 300 mmHg, about 10 to about 350 mmHg, about 10 mmHg to about 400 mmHg, about 20 mmHg to about 30 mmHg, about 20 mmHg to about 40 mmHg, about 20 mmHg to about 50 mmHg, about 20 mmHg to about 60 mmHg, about 20 mmHg to about 70 mmHg, about 20 mmHg to about 80 mmHg, about 20 mmHg to about 90 mmHg, about 20 mmHg to about 100 mmHg, about 20 mmHg to about 110 mmHg, about 20 mmHg to about 120 mmHg, about 20 mmHg to about 130 mmHg, about 20 mmHg to about 140 mmHg, about 20 mmHg to about 150 mmHg, about 20 mmHg to about 175 mmHg, about 20 mmHg to about 200 mmHg, about 20 mmHg to about 225 mmHg, about 20 mmHg to about 250 mmHg, about 20 mmHg to about 300 mmHg, about 20 to about 350 mmHg, about 20 mmHg to about 400 mmHg, about 25 mmHg to about 50 mmHg, about 25 mmHg to about 75 mmHg, about 25 mmHg to about 100 mmHg, about 30 mmHg to about 40 mmHg, about 30 mmHg to about 50 mmHg, about 30 mmHg to about 60 mmHg, about 30 mmHg to about 70 mmHg, about 30 mmHg to about 80 mmHg, about 30 mmHg to about 90 mmHg, about 30 mmHg to about 100 mmHg, about 30 mmHg to about 110 mmHg, about 30 mmHg to about 120 mmHg, about 30 mmHg to about 130 mmHg, about 30 mmHg to about 140 mmHg, about 30 mmHg to about 150 mmHg, about 30 mmHg to about 175 mmHg, about 30 mmHg to about 200 mmHg, about 30 mmHg to about 225 mmHg, about 30 mmHg to about 250 mmHg, about 30 mmHg to about 300 mmHg, about 30 to about 350 mmHg, about 30 mmHg to about 400 mmHg, about 40 mmHg to about 50 mmHg, about 40 mmHg to about 60 mmHg, about 40 mmHg to about 70 mmHg, about 40 mmHg to about 80 mmHg, about 40 mmHg to about 90 mmHg, about 40 mmHg to about 100 mmHg, about 40 mmHg to about 110 mmHg, about 40 mmHg to about 120 mmHg, about 40 mmHg to about 130 mmHg, about 40 mmHg to about 140 mmHg, about 40 mmHg to about 150 mmHg, about 40 mmHg to about 175 mmHg, about 40 mmHg to about 200 mmHg, about 40 mmHg to about 225 mmHg, about 40 mmHg to about 250 mmHg, about 40 mmHg to about 300 mmHg, about 40 to about 350 mmHg, about 40 mmHg to about 400 mmHg, about 50 mmHg to about 60 mmHg, about 50 mmHg to about 70 mmHg, about 50 mmHg to about 75 mmHg, about 50 mmHg to about 80 mmHg, about 50 mmHg to about 90 mmHg, about 50 mmHg to about 100 mmHg, about 50 mmHg to about 110 mmHg, about 50 mmHg to about 120 mmHg, about 50 mmHg to about 130 mmHg, about mmHg 50 to about 140 mmHg, about 50 mmHg to about 150 mmHg, about 50 mmHg to about 175 mmHg, about 50 mmHg to about 200 mmHg, about 50 mmHg to about 225 mmHg, about 50 mmHg to about 250 mmHg, about 50 mmHg to about 300 mmHg, about 50 to about 350 mmHg, about 50 mmHg to about 400 mmHg, about 60 mmHg to about 70 mmHg, about 60 mmHg to about 80 mmHg, about 60 mmHg to about 90 mmHg, about 60 mmHg to about 100 mmHg, about 60 mmHg to about 110 mmHg, about 60 mmHg to about 120 mmHg, about 60 mmHg to about 130 mmHg, about 60 mmHg to about 140 mmHg, about 60 mmHg to about 150 mmHg, about 60 mmHg to about 175 mmHg, about 60 mmHg to about 200 mmHg, about 60 mmHg to about 225 mmHg, about 60 mmHg to about 250 mmHg, about 60 mmHg to about 300 mmHg, about 60 to about 350 mmHg, about 60 mmHg to about 400 mmHg, about 70 mmHg to about 80 mmHg, about 70 mmHg to about 90 mmHg, about 70 mmHg to about 100 mmHg, about 70 mmHg to about 110 mmHg, about 70 mmHg to about 120 mmHg, about 70 mmHg to about 130 mmHg, about 70 mmHg to about 140 mmHg, about 70 mmHg to about 150 mmHg, about 70 mmHg to about 175 mmHg, about 70 mmHg to about 200 mmHg, about 70 mmHg to about 225 mmHg, about 70 mmHg to about 250 mmHg, about 70 mmHg to about 300 mmHg, about 70 to about 350 mmHg, about 70 mmHg to about 400 mmHg, about 75 mmHg to about 100 mmHg, about 75 mmHg to about 125 mmHg, about 80 mmHg to about 90 mmHg, about 80 mmHg to about 100 mmHg, about 80 mmHg to about 110 mmHg, about 80 mmHg to about 120 mmHg, about 80 mmHg to about 130 mmHg, about 80 mmHg to about 140 mmHg, about 80 mmHg to about 150 mmHg, about 80 mmHg to about 175 mmHg, about 80 mmHg to about 200 mmHg, about 80 mmHg to about 225 mmHg, about 80 mmHg to about 250 mmHg, about 80 mmHg to about 300 mmHg, about 80 to about 350 mmHg, about 80 mmHg to about 400 mmHg, about 90 mmHg to about 100 mmHg, about 90 mmHg to about 110 mmHg, about 90 mmHg to about 120 mmHg, about 90 mmHg to about 130 mmHg, about 90 mmHg to about 140 mmHg, about 90 mmHg to about 150 mmHg, about 90 mmHg to about 175 mmHg, about 90 mmHg to about 200 mmHg, about 90 mmHg to about 225 mmHg, about 90 mmHg to about 250 mmHg, about 90 mmHg to about 300 mmHg, about 90 to about 350 mmHg, about 90 mmHg to about 400 mmHg, about 100 mmHg to about 110 mmHg, about 100 mmHg to about 120 mmHg, about 100 mmHg to about 130 mmHg, about 100 mmHg to about 140 mmHg, about 100 mmHg to about 150 mmHg, about 100 mmHg to about 175 mmHg, about 100 mmHg to about 200 mmHg, about 100 mmHg to about 225 mmHg, about 100 mmHg to about 250 mmHg, about 100 mmHg to about 300 mmHg, about 100 to about 350 mmHg, about 100 mmHg to about 400 mmHg, about 110 mmHg to about 120 mmHg, about 110 mmHg to about 130 mmHg, about 110 mmHg to about 140 mmHg, about 110 mmHg to about 150 mmHg, about 110 mmHg to about 175 mmHg, about 110 mmHg to about 200 mmHg, about 110 mmHg to about 225 mmHg, about 110 mmHg to about 250 mmHg, about 110 mmHg to about 300 mmHg, about 110 to about 350 mmHg, about 110 mmHg to about 400 mmHg, about 120 mmHg to about 130 mmHg, about 120 mmHg to about 140 mmHg, about 120 mmHg to about 150 mmHg, about 120 mmHg to about 175 mmHg, about 120 mmHg to about 200 mmHg, about 120 mmHg to about 225 mmHg, about 120 mmHg to about 250 mmHg, about 120 mmHg to about 300 mmHg, about 120 to about 350 mmHg, about 120 mmHg to about 400 mmHg, about 130 mmHg to about 140 mmHg, about 130 mmHg to about 150 mmHg, about 130 mmHg to about 175 mmHg, about 130 mmHg to about 200 mmHg, about 130 mmHg to about 225 mmHg, about 130 mmHg to about 250 mmHg, about 130 mmHg to about 300 mmHg, about 130 to about 350 mmHg, about 130 mmHg to about 400 mmHg, about 140 mmHg to about 150 mmHg, about 140 mmHg to about 175 mmHg, about 140 mmHg to about 200 mmHg, about 140 mmHg to about 225 mmHg, about 140 mmHg to about 250 mmHg, about 140 mmHg to about 300 mmHg, about 140 to about 350 mmHg, about 140 mmHg to about 400 mmHg, about 150 mmHg to about 175 mmHg, about 150 mmHg to about 200 mmHg, about 150 mmHg to about 225 mmHg, about 150 mmHg to about 250 mmHg, about 150 mmHg to about 300 mmHg, about 150 to about 350 mmHg, about 150 mmHg to about 400 mmHg, about 175 mmHg to about 200 mmHg, about 175 mmHg to about 225 mmHg, about 175 mmHg to about 250 mmHg, about 175 mmHg to about 300 mmHg, about 175 to about 350 mmHg, about 175 mmHg to about 400 mmHg, about 200 mmHg to about 225 mmHg, about 200 mmHg to about 250 mmHg, about 200 mmHg to about 300 mmHg, about 200 to about 350 mmHg, about 200 mmHg to about 400 mmHg, about 225 mmHg to about 250 mmHg, about 225 mmHg to about 300 mmHg, about 225 to about 350 mmHg, about 225 mmHg to about 400 mmHg, about 275 mmHg to about 300 mmHg, about 275 to about 350 mmHg, about 275 mmHg to about 400 mmHg, about 300 mmHg to about 325 mmHg, about 300 to about 350 mmHg, about 300 mmHg to about 400 mmHg, about 325 mmHg to about 350 mmHg, about 325 to about 375 mmHg, about 325 mmHg to about 400 mmHg, about 350 mmHg to about 375 mmHg, about 350 to about 400 mmHg, or about 375 mmHg to about 400 mmHg.

In some embodiments, pressure applied to the breast cup (2) may change, e.g., from about every seconds to about every 120 seconds (e.g., about every 0.1 seconds to about every 1 second, about every 0.1 seconds to about every 2 seconds, about every 0.1 seconds to about every 3 seconds, about every 0.1 seconds to about every 4 seconds, about every 0.1 seconds to about every 5 seconds, about every 0.1 seconds to about every 6 seconds, about every 0.1 seconds to about every 7 seconds, about every 0.1 seconds to about every 8 seconds, about every 0.1 seconds to about every 9 seconds, about every 0.1 seconds to about every 10 seconds, about every 0.1 seconds to about every 11 seconds, about every 0.1 seconds to about every 12 seconds, about every 0.1 seconds to about every 13 seconds, about every 0.1 seconds to about every 14 seconds, about every 0.1 seconds to about every 15 seconds, about every 0.1 seconds to about every 20 seconds, about every 0.1 seconds to about every 30 seconds, about every 0.1 seconds to about every 45 seconds, about every 0.1 seconds to about every 60 seconds, about every 0.1 seconds to about every 90 seconds, about every 1 second to about every 2 seconds, about every 1 second to about every 3 seconds, about every 1 second to about every 4 seconds, about every 1 second to about every 5 seconds, about every 1 second to about every 6 seconds, about every 1 second to about every 7 seconds, about every 1 second to about every 8 seconds, about every 1 second to about every 9 seconds, about every 1 second to about every 10 seconds, about every 2 second to about every seconds, about every 3 second to about every 7 seconds, about every 4 second to about every 5 seconds, about every 5 second to about every 10 seconds, about every 10 second to about every 15 seconds, about every 15 second to about every 30 seconds, about every 0.1 seconds, about every 0.2 seconds, about every 0.3 seconds, about every 0.4 seconds, about every 0.5 seconds, about every 0.6 seconds, about every 0.7 seconds, about every 0.8 seconds, about every 0.9 seconds, about every 1 second, about every 1.5 seconds, about every 2 seconds, about every 3 seconds, about every 4 seconds, about every 5 seconds, about every 6 seconds, about every 7 seconds, about every 8 seconds, about every 9 seconds, about every 10 seconds, about every 11 seconds, about every 12 seconds, about every 13 seconds, about every 14 seconds, about every 15 seconds, about every 20 seconds, about every 30 seconds, about every 45 seconds, about every 60 seconds, about every 75 seconds, about every 90 seconds, about every 105 seconds, or about every 120 seconds).

In some embodiments, pressure applied to the breast cup (2) changes gradually. In some embodiments, pressure applied to the breast cup (2) changes at different rates, e.g., in a first cycle the pressure applied to the breast cup (2) changes over about 0.1 seconds to about 120 seconds (e.g., about 1 second), and in a second cycle the pressure applied to the breast cup (2) changes over about 0.1 seconds to about 120 seconds (e.g., about 5 seconds).

Pressure within the breast cup (2) can provide a pulsating or massaging sensation. In some embodiments, the speed and pressure of the pulsation or massage may be selected by the user. In some embodiments, alternating pressure mimics the action of suckling.

Additional Elements

In some embodiments, the breast milk distribution system (1) includes a pressure outlet. The pressure outlet may or may not include a valve (24). In some embodiments, each pressure outlet includes a valve (24). In some embodiments, the pressure outlet is a breather tube. In some embodiments, the pressure outlet is an orifice, e.g., the reservoir (3) or the lid of the reservoir (3) may include an orifice. In some embodiments, the breast milk distribution system (1) includes a pressure outlet in fluidic communication with each reservoir (3).

In some embodiments, the reservoir (3) includes a pressure indicator, e.g., a flexible membrane. A pressure indicator, e.g., a flexible membrane, may be advantageous in indicating if there is negative or positive pressure within the reservoir (3). Negative pressure may be the result of hot milk being cooled when the reservoir (3) is closed to the ambient atmosphere and/or the breast milk distribution system (1).

In some embodiments, the breast milk distribution system (1) includes a waste reservoir. In some embodiments, following a breast pumping session, the breast milk distribution system (1) may flush the system with a cleaning fluid, wherein the cleaning fluid is transported to a waste reservoir. In some embodiments, the cleaning fluid is water. In some embodiments, the cleaning fluid is air. In some embodiments, the breast milk distribution system (1) is configured to be flushed with a pressure source, e.g., positive pressure source or a negative pressure source, e.g., a vacuum pump.

In some embodiments, the breast milk distribution system (1) may include an anti-bacterial coating, e.g., in the reservoir (3) or the fluid conduits (5).

The breast milk distribution system (1) may include a power source (12). The power source (12) may be a battery and/or an AC power source. The power source (12) may be electrically connected to the control unit and the pumping mechanism.

The breast milk distribution system (1) may include a display. The display may be disposed on the pump housing (7) or reservoir enclosure (4). The display may be a screen. In some embodiments, the screen is a touchscreen.

The breast milk distribution system (1) may include a timer. The drive unit (11) and/or control unit may include the timer. The timer may be disposed in the pump housing (7) or reservoir enclosure (4).

The breast milk distribution system (1) may include an alarm. The alarm may be disposed in the pump housing (7) or reservoir enclosure (4). The alarm may be a light, a vibration element, or a sound element. The alarm may be configured to sound in the event of an error (e.g., the pumping system is improperly assembled), the ending of a pumping session, a temperature increase in the milk in the reservoir (3), a full reservoir (3), and/or the start of an upcoming preprogrammed pumping session.

The breast milk distribution system (1) may include a power switch (14) or button. The power switch (14) or button may enable a user to power on or off the breast milk distribution system (1). The power switch (14) or button may be disposed on the outside of the pump housing (7). Alternatively, or in addition, the power switch (14) or button may be disposed on the reservoir enclosure (4). However, in some embodiments, the user may power on or off the breast milk distribution system (1) remotely, such as through an application on an external computer, e.g., a mobile device.

Breast Milk Distribution System Control

The breast milk distribution system may include controls that are operable by a user to select or modify at least one of: pumping program or mode, frequency of pumping cycle, maximum suction pressure achieved during a pumping cycle, latch suction pressure achieved during the pumping cycle, pumping force, pumping session time, and distribution of milk to reservoirs (3). The controls may be present on the surface of the pump housing (7) or reservoir enclosure (4), e.g., on the display. Alternatively, or in addition, the controls may be present in an application on an external computer, e.g., a mobile device. Alternatively, neither the pump housing (7) or reservoir enclosure (4) includes controls, and the breast milk distribution system (1) is solely controlled through an application on an external computer, e.g., a mobile device. Control of the breast milk distribution system through an application on an external computer is advantageous in that a user may control the device in any position.

In some embodiments, the breast milk distribution system can have a wait time set, e.g., through the display or an application on an external computer, such that the user has time to contact the breast cup (2) to their breast before the system begins pumping.

Control of the breast milk distribution system (1) may be customized. The customized pump functions include modifications to at least one of: maximum suction pressure level, latch suction pressure level, suction pressure waveform over a pumping cycle, phases of extraction or feeding times, rest times, heating temperatures and times, vibration frequency and duration, pumping session time, and distribution of milk to reservoirs (3). The user may input at least one pump program into the breast milk distribution system (1), e.g., through the display or application on an external computer. For example, the user may set the number of minutes that the breast milk distribution system (1) will run before shutting off automatically and/or the user may set a time for the breast milk distribution system (1) to engage during the night. Custom pump programming is advantageous in that user may control how long they pump for so that they may go about their daily activities, resting, or sleeping, without the worry that the pump will continue endlessly. In some embodiments, the pumping frequency may be programmed to slow down gradually during operation, e.g., towards the end of a preprogrammed pumping time.

Wireless

The control unit may be configured to send signals to and receive signals from an external computer, e.g., a mobile device.

The control unit may include a transmission element, e.g., a wireless transmission element, and receiver element for wirelessly sending signal to and receiving signals from the external computer. In some embodiments, the transmission element is a BLUETOOTH® transmission element.

The external computer may include a processor and instructions, which when executed, cause the processor to customize pump functions and send customized pump functions to the control unit. In some embodiments, the custom pump functions are based on the signals received from the control unit, such as measurements taken by sensors. In some embodiments, the user is able to program different custom pump programs, e.g., a daytime program and a nighttime program.

The external computer may include a processor and Instructions, which when executed, cause the processor to calculate volume of milk extracted and track expression efficiency and monitor it over time. In some embodiments, the calculation of milk extracted, and expression efficiency are based on signals received from the control unit, such as measurements taken by the sensors.

The external computer may include a processor and instructions, which when executed, cause the processor to transport milk from a breast pumping session to a reservoir, including transporting milk from a first breast pumping session to a first reservoir, and milk from a second breast pumping session to a second reservoir.

The external computer may include a processor and instructions, which when executed, cause the processor to track of inventory of previous pumping sessions, including tracking at least one of dates of the previous pumping sessions, volumes pumped in the previous pumping sessions, and specific tracking numbers for specific milk collection containers into which milk has been pumped in the previous pumping sessions.

The external computer may include a processor and instructions, which when executed, cause the processor to one or more of monitor remaining battery power of the battery and output a warning when the battery reaches a predetermined low level of charge.

The external computer may include a processor and instructions, which when executed, cause the processor to display in the application screen or on display of the breast milk distribution system (1) the time left in the pumping session, measurements taken by the at least one sensor, and/or one or more photos of the user's choosing on the display.

Methods of Use

The present disclosure provides improved methods of collecting and distributing pumped breast milk.

The present disclosure provides a method of breast milk distribution by: (i) providing a breast milk distribution system of the disclosure; (ii) pumping milk from a human breast using breast cup; and (iii) applying pressure to move milk from the breast cup to the reservoir (3).

In some embodiments, the method includes transporting milk through the first fluid conduit. In some embodiments, the method includes transporting milk through the one directional valve. In some embodiments, the method includes applying pressure to the manifold (6) with a pressure source to transport milk to a reservoir (3). Thus, in some embodiments, the pressure source, or a second pressure source, can be in fluidic communication with the manifold (6). In some embodiments, a positive pressure source is in fluidic communication with the manifold (6) and transports milk to a reservoir (3). In some embodiments, the method includes applying a negative pressure source to the breast cup at the end of the pumping session. In this embodiment, the negative pressure transports any residual milk from the breast cup and fluid conduit (5) into the reservoir (3). In some embodiments, the negative pressure source is a peristaltic pump, e.g., on a first conduit or downstream component connected thereto. Positive pressure may also be introduced into the breast cup, e.g., via a separate inlet, to aid in transport of milk or cleaning. The clearing of milk from the fluid conduit and/or breast cup may occur only once at the end of a breast pumping cycle.

In some embodiments, the method includes providing a cleaning fluid to the breast milk distribution system (1). In some embodiments, the method includes transporting a cleaning fluid from the breast cup (2) to a waste reservoir (3). In some embodiments, the cleaning fluid is transported through the manifold (6). In some embodiments, the cleaning fluid is water. In some embodiments, the method includes pumping milk from the human breast twice, in which there is at least 30 minutes from a first breast pumping session to a second breast pumping session. In some embodiments, the method includes pumping milk from the human breast 1, 2, 3, 4, 5, 6, 7, 8, 9, or 10 times. In some embodiments, the method includes pumping milk from the human breast a plurality of times (e.g., from 2 to 3 times, from 2 to 4 times, from 2 to 5 times, from 2 to 6 times, from 2 to 10 times, from 3 to 4 times, from 3 to 5 times, from 3 to 10 times, from 4 to 5 times, from 4 to 6 times, or from 5 to 10 times).

In some embodiments, the time between one breast pumping session and another breast pumping session (e.g., between a first breast pumping session and a second breast pumping session, a second breast pumping session and a third breast pumping session, a third breast pumping session and a fourth breast pumping session, etc.) is from about 30 minutes to about 240 minutes (e.g., about 30 minutes to about 45 minutes, about 30 minutes to about 60 minutes, about 30 minutes to about 90 minutes, about 30 minutes to about 120 minutes, about 30 minutes to about 180 minutes, about 45 minutes to about 60 minutes, about 45 minutes to about 90 minutes, about 45 minutes to about 120 minutes, about 60 minutes to about 90 minutes, about 60 minutes to about 120 minutes, about 50 minutes to about 180 minutes, about 60 minutes to about 210 minutes, about 90 minutes to about 120 minutes, about 90 minutes to about 180 minutes, about 90 minutes to about 210 minutes, about 90 minutes to about 240 minutes, about 120 minutes to about 180 minutes, about 120 minutes to about 210 minutes, about 120 minutes to about 240 minutes, about 180 minutes to about 210 minutes, about 180 minutes to about 240 minutes, about 210 minutes to about 240 minutes, about 30 minutes, about 45 minutes, about 60 minutes, about 85 minutes, about 90 minutes, about 105 minutes, about 120 minutes, about 135 minutes, about 150 minutes, about 165 minutes, about 180 minutes, about 195 minutes, about 210 minutes, about 225 minutes, or about 240 minutes). In some embodiments, the breast milk distribution system (1) may enter a waiting phase between breast pumping sessions where the breast cup (2) and/or manifold (6) is not in fluidic communication with any reservoir (3). In some embodiments, following a breast pumping session, the breast milk distribution system (1) places the breast cup (2) and/or manifold (6) in fluidic communication with a second reservoir (3). The second reservoir (3) may be empty.

In some embodiments, milk from the first breast pumping session is transported to a first reservoir, and milk from the second breast pumping session is transported to a second reservoir. Likewise, milk from a third, fourth, fifth, sixth, seventh, eighth, ninth, or tenth breast pumping session may be transported into a third, fourth, fifth, sixth, seventh, eighth, ninth, or tenth reservoir, respectively. In some embodiments, the method includes removing fluidic communication between the breast cup (2) and all of the reservoirs (3) between breast pumping sessions. In some embodiments, a plurality of valves is closed to remove fluidic communication between the breast cup (2) and all of the reservoirs (3). Once full, a reservoir may be removed and replaced with an empty reservoir.

The breast milk distribution system (1) is advantageous in that the user may be able to breast pump a plurality of times following a one-time assembly. Prior to the first use, the user may secure the breast cup to a breast. Then, in some embodiments, the user does not need to remove the breast cup (2) between a plurality of breast pumping sessions, e.g., two, three, four, five, six, seven, eight, nine, or ten breast pumping sessions. The breast milk distribution system (1) is further advantageous in that the user may be able to breast pump in a reclined position. As the breast milk distribution system (1) may be used for an extended time, e.g., overnight, the user's ability to place the wearable component on one time, yet still use the pump several times without removal of the garment will allow for uninterrupted sleep during at least one breast pumping session. A pre-programmed pumping schedule may initiate the breast milk distribution system (1) at least once, e.g., two, three, four, five, six, seven, eight, nine, ten times, etc. In some embodiments, the breast milk distribution system (1) can distinguish between pumping sessions based on the pre-programmed breast pumping schedule. For example, on the initiation of a new breast pumping session, the breast milk distribution system (1) can divert the milk flow via a manifold (6) to an empty reservoir (3).

In some embodiments, the method includes pumping milk from the human breast to induce milk from a first breast pumping session to flow from a nipple to the manifold via the breast cup (2); providing fluidic communication between the inlet (8) of the manifold (6) and a first reservoir (3) to allow milk from the first breast pumping session to flow into the first reservoir (3); removing fluidic communication between the inlet (8) of the manifold (6) and the first fluid reservoir (3); pumping the human breast to induce milk from a second breast pumping session to flow from the nipple to the manifold (6) via the breast cup (2); and providing fluidic communication between the inlet (8) of the manifold (6) and a second reservoir (3) to allow milk from the second breast pumping session to flow into the second reservoir (3). In some embodiments, the time between first and second pumping sessions is from about 30 minutes to about 240 minutes (e.g., about 30 minutes to about 45 minutes, about 30 minutes to about 60 minutes, about 30 minutes to about 90 minutes, about 30 minutes to about 120 minutes, about 30 minutes to about 180 minutes, about 45 minutes to about 60 minutes, about 45 minutes to about 90 minutes, about 45 minutes to about 120 minutes, about 60 minutes to about 90 minutes, about 60 minutes to about 120 minutes, about 50 minutes to about 180 minutes, about 60 minutes to about 210 minutes, about 90 minutes to about 120 minutes, about 90 minutes to about 180 minutes, about 90 minutes to about 210 minutes, about 90 minutes to about 240 minutes, about 120 minutes to about 180 minutes, about 120 minutes to about 210 minutes, about 120 minutes to about 240 minutes, about 180 minutes to about 210 minutes, about 180 minutes to about 240 minutes, about 210 minutes to about 240 minutes, about 30 minutes, about 45 minutes, about 60 minutes, about 85 minutes, about 90 minutes, about 105 minutes, about 120 minutes, about 135 minutes, about 150 minutes, about 165 minutes, about 180 minutes, about 195 minutes, about 210 minutes, about 225 minutes, or about 240 minutes).

In some embodiments, the method further includes removing fluidic communication between the inlet (8) of the manifold (6) and the second fluid reservoir (3); and providing fluidic communication between the inlet (8) of the manifold (6) and a third reservoir (3); and pumping the human breast to induce milk from a third breast pumping session to flow from the nipple to the manifold (6) via the breast cup (2). In some embodiments, the time between second and third pumping sessions is from 30 minutes to 240 minutes (e.g., about 30 minutes to about 45 minutes, about 30 minutes to about 60 minutes, about minutes to about 90 minutes, about 30 minutes to about 120 minutes, about 30 minutes to about 180 minutes, about 45 minutes to about 60 minutes, about 45 minutes to about 90 minutes, about 45 minutes to about 120 minutes, about 60 minutes to about 90 minutes, about 60 minutes to about 120 minutes, about 50 minutes to about 180 minutes, about 60 minutes to about 210 minutes, about 90 minutes to about 120 minutes, about 90 minutes to about 180 minutes, about 90 minutes to about 210 minutes, about 90 minutes to about 240 minutes, about 120 minutes to about 180 minutes, about 120 minutes to about 210 minutes, about 120 minutes to about 240 minutes, about 180 minutes to about 210 minutes, about 180 minutes to about 240 minutes, about 210 minutes to about 240 minutes, about 30 minutes, about 45 minutes, about 60 minutes, about 85 minutes, about 90 minutes, about 105 minutes, about 120 minutes, about 135 minutes, about 150 minutes, about 165 minutes, about 180 minutes, about 195 minutes, about 210 minutes, about 225 minutes, or about 240 minutes).

In some embodiments, the method further includes providing fluidic communication between (i) the inlet (8) of the manifold (6) and (ii) the first reservoir (3), the second reservoir (3), or the third fluid reservoir (3) by moving, e.g., rotating, the movable, e.g., rotating, member. In some embodiments, the method further includes removing fluidic communication between (i) the inlet of the manifold and (ii) the first reservoir (3), the second reservoir (3), or the third fluid reservoir (3) by moving, e.g., rotating, the movable, e.g., rotating, member. In some embodiments, the movable, e.g., rotating, member moves clockwise with respect to the stationary member. In some embodiments, the movable, e.g., rotating, member moves counterclockwise with respect to the stationary member.

In some embodiments, the method further includes providing fluidic communication between (i) the inlet of the manifold (6) and (ii) the first reservoir (3), the second reservoir (3), or the third fluid reservoir (3) by opening the valve to the inlet of the first reservoir (3), the second reservoir (3), or the third fluid reservoir (3). In some embodiments, the method further includes removing fluidic communication between (i) the inlet (8) of the manifold (6) and (ii) the first reservoir (3), the second reservoir (3), or the third fluid reservoir (3) by closing the valve (24) to the inlet of the first reservoir (3), the second reservoir (3), or the third fluid reservoir (3).

In some embodiments, the method further includes providing fluidic communication between (i) the inlet of the manifold (6) and (ii) the first reservoir (3), the second reservoir (3), or the third fluid reservoir (3) by moving the arm. In some embodiments, the method further includes removing fluidic communication between (i) the inlet of the manifold (6) and (ii) the first reservoir (3), the second reservoir (3), or the third fluid reservoir (3) by moving the arm. In some embodiments, the method further includes moving the arm with the drive unit (11), wherein the drive unit (11) is the stepper motor.

In some embodiments, the method further includes turning on the breast milk distribution system (1). The breast milk distribution system (1) may be turned on after the breast cup (2) is contacted to the human breast. In some embodiments, the breast milk distribution system (1) may be turned on before the breast cup (2) is contacted to the human breast, e.g., the negative pressure is applied after the human breast is contacted, or the human breast is contacted during a waiting period before the negative pressure is applied. In some embodiments, the breast milk distribution system (1) is turned on with the power switch (14). In some embodiments, the breast milk distribution system (1) is turned on remotely. In some embodiments, the breast milk distribution system (1) is turned on automatically according to a pre-programmed schedule. In some embodiments, the breast milk distribution system (1) is turned on automatically according to a pre-programmed schedule a plurality of times.

In some embodiments, the method further includes turning on a pressure source. A pressure source may be turned on after the breast cup (2) contacts the human breast. In some embodiments, the pressure source is turned on with the power switch (14). In some embodiments, the pressure source is turned on remotely. In some embodiments, the pressure source is turned on automatically according to a pre-programmed schedule. In some embodiments, the pressure source is turned on automatically according to a pre-programmed schedule a plurality of times. The pressure source may be the negative pressure source (9) or a positive pressure source.

In some embodiments, the method further includes turning on the negative pressure source (9). The negative pressure source (9) may be turned on after the breast cup (2) is contacted to the human breast. In some embodiments, negative pressure source (9) is turned on with the power switch (14). In some embodiments, the negative pressure source (9) is turned on remotely. In some embodiments, the negative pressure source (9) is turned on automatically according to a pre-programmed schedule. In some embodiments, the negative pressure source (9) is turned on automatically according to a pre-programmed schedule a plurality of times.

The first pressure or second pressure may be between about 0 mmHg to about 250 mmHg, e.g., about 0 mmHg to about 10 mmHg, about 0 mmHg to about 20 mmHg, about 0 mmHg to about 30 mmHg, about 0 mmHg to about 40 mmHg, about 0 mmHg to about 50 mmHg, about 0 mmHg to about 60 mmHg, about 0 mmHg to about 70 mmHg, about 0 mmHg to about 80 mmHg, about 0 mmHg to about 90 mmHg, about 0 to about 100 mmHg, about 0 mmHg to about 110 mmHg, about 0 mmHg to about 120 mmHg, about 0 mmHg to about 130 mmHg, about 0 to about 140 mmHg, about 0 mmHg to about 150 mmHg, about 0 to about 175 mmHg, about 0 mmHg to about 200 mmHg, about 0 mmHg to about 225 mmHg, about 0 mmHg to about 250 mmHg, about 0 mmHg to about 275 mmHg, about 0 mmHg to about 300 mmHg, about 0 to about 350 mmHg, about 0 mmHg to about 400 mmHg, about 10 mmHg to about 20 mmHg, about 10 mmHg to about 30 mmHg, about 10 mmHg to about 40 mmHg, about 10 mmHg to about 50 mmHg, about 10 mmHg to about 60 mmHg, about 10 mmHg to about 70 mmHg, about 10 mmHg to about 80 mmHg, about 10 mmHg to about 90 mmHg, about 10 mmHg to about 100 mmHg, about 10 mmHg to about 110 mmHg, about 10 mmHg to about 120 mmHg, about 10 mmHg to about 130 mmHg, about 10 mmHg to about 140 mmHg, about 10 mmHg to about 150 mmHg, about 10 mmHg to about 175 mmHg, about 10 mmHg to about 200 mmHg, about 10 mmHg to about 225 mmHg, about 10 mmHg to about 250 mmHg, about 10 mmHg to about 300 mmHg, about 10 to about 350 mmHg, about 10 mmHg to about 400 mmHg, about 20 mmHg to about 30 mmHg, about 20 mmHg to about 40 mmHg, about 20 mmHg to about 50 mmHg, about 20 mmHg to about 60 mmHg, about 20 mmHg to about 70 mmHg, about 20 mmHg to about 80 mmHg, about 20 mmHg to about 90 mmHg, about 20 mmHg to about 100 mmHg, about 20 mmHg to about 110 mmHg, about 20 mmHg to about 120 mmHg, about 20 mmHg to about 130 mmHg, about 20 mmHg to about 140 mmHg, about 20 mmHg to about 150 mmHg, about 20 mmHg to about 175 mmHg, about 20 mmHg to about 200 mmHg, about 20 mmHg to about 225 mmHg, about 20 mmHg to about 250 mmHg, about 20 mmHg to about 300 mmHg, about 20 to about 350 mmHg, about 20 mmHg to about 400 mmHg, about 25 mmHg to about 50 mmHg, about 25 mmHg to about 75 mmHg, about 25 mmHg to about 100 mmHg, about 30 mmHg to about 40 mmHg, about 30 mmHg to about 50 mmHg, about 30 mmHg to about 60 mmHg, about 30 mmHg to about 70 mmHg, about 30 mmHg to about 80 mmHg, about 30 mmHg to about 90 mmHg, about 30 mmHg to about 100 mmHg, about 30 mmHg to about 110 mmHg, about 30 mmHg to about 120 mmHg, about 30 mmHg to about 130 mmHg, about 30 mmHg to about 140 mmHg, about 30 mmHg to about 150 mmHg, about 30 mmHg to about 175 mmHg, about 30 mmHg to about 200 mmHg, about 30 mmHg to about 225 mmHg, about 30 mmHg to about 250 mmHg, about 30 mmHg to about 300 mmHg, about 30 to about 350 mmHg, about 30 mmHg to about 400 mmHg, about 40 mmHg to about 50 mmHg, about 40 mmHg to about 60 mmHg, about 40 mmHg to about 70 mmHg, about 40 mmHg to about 80 mmHg, about 40 mmHg to about 90 mmHg, about 40 mmHg to about 100 mmHg, about 40 mmHg to about 110 mmHg, about 40 mmHg to about 120 mmHg, about 40 mmHg to about 130 mmHg, about 40 mmHg to about 140 mmHg, about 40 mmHg to about 150 mmHg, about 40 mmHg to about 175 mmHg, about 40 mmHg to about 200 mmHg, about 40 mmHg to about 225 mmHg, about 40 mmHg to about 250 mmHg, about 40 mmHg to about 300 mmHg, about 40 to about 350 mmHg, about 40 mmHg to about 400 mmHg, about 50 mmHg to about 60 mmHg, about 50 mmHg to about 70 mmHg, about 50 mmHg to about 75 mmHg, about 50 mmHg to about 80 mmHg, about 50 mmHg to about 90 mmHg, about 50 mmHg to about 100 mmHg, about 50 mmHg to about 110 mmHg, about 50 mmHg to about 120 mmHg, about 50 mmHg to about 130 mmHg, about mmHg 50 to about 140 mmHg, about 50 mmHg to about 150 mmHg, about 50 mmHg to about 175 mmHg, about 50 mmHg to about 200 mmHg, about 50 mmHg to about 225 mmHg, about 50 mmHg to about 250 mmHg, about 50 mmHg to about 300 mmHg, about 50 to about 350 mmHg, about 50 mmHg to about 400 mmHg, about 60 mmHg to about 70 mmHg, about 60 mmHg to about 80 mmHg, about 60 mmHg to about 90 mmHg, about 60 mmHg to about 100 mmHg, about 60 mmHg to about 110 mmHg, about 60 mmHg to about 120 mmHg, about 60 mmHg to about 130 mmHg, about 60 mmHg to about 140 mmHg, about 60 mmHg to about 150 mmHg, about 60 mmHg to about 175 mmHg, about 60 mmHg to about 200 mmHg, about 60 mmHg to about 225 mmHg, about 60 mmHg to about 250 mmHg, about 60 mmHg to about 300 mmHg, about 60 to about 350 mmHg, about 60 mmHg to about 400 mmHg, about 70 mmHg to about 80 mmHg, about 70 mmHg to about 90 mmHg, about 70 mmHg to about 100 mmHg, about 70 mmHg to about 110 mmHg, about 70 mmHg to about 120 mmHg, about 70 mmHg to about 130 mmHg, about 70 mmHg to about 140 mmHg, about 70 mmHg to about 150 mmHg, about 70 mmHg to about 175 mmHg, about 70 mmHg to about 200 mmHg, about 70 mmHg to about 225 mmHg, about 70 mmHg to about 250 mmHg, about 70 mmHg to about 300 mmHg, about 70 to about 350 mmHg, about 70 mmHg to about 400 mmHg, about 75 mmHg to about 100 mmHg, about 75 mmHg to about 125 mmHg, about 80 mmHg to about 90 mmHg, about 80 mmHg to about 100 mmHg, about 80 mmHg to about 110 mmHg, about 80 mmHg to about 120 mmHg, about 80 mmHg to about 130 mmHg, about 80 mmHg to about 140 mmHg, about 80 mmHg to about 150 mmHg, about 80 mmHg to about 175 mmHg, about 80 mmHg to about 200 mmHg, about 80 mmHg to about 225 mmHg, about 80 mmHg to about 250 mmHg, about 80 mmHg to about 300 mmHg, about 80 to about 350 mmHg, about 80 mmHg to about 400 mmHg, about 90 mmHg to about 100 mmHg, about 90 mmHg to about 110 mmHg, about 90 mmHg to about 120 mmHg, about 90 mmHg to about 130 mmHg, about 90 mmHg to about 140 mmHg, about 90 mmHg to about 150 mmHg, about 90 mmHg to about 175 mmHg, about 90 mmHg to about 200 mmHg, about 90 mmHg to about 225 mmHg, about 90 mmHg to about 250 mmHg, about 90 mmHg to about 300 mmHg, about 90 to about 350 mmHg, about 90 mmHg to about 400 mmHg, about 100 mmHg to about 110 mmHg, about 100 mmHg to about 120 mmHg, about 100 mmHg to about 130 mmHg, about 100 mmHg to about 140 mmHg, about 100 mmHg to about 150 mmHg, about 100 mmHg to about 175 mmHg, about 100 mmHg to about 200 mmHg, about 100 mmHg to about 225 mmHg, about 100 mmHg to about 250 mmHg, about 100 mmHg to about 300 mmHg, about 100 to about 350 mmHg, about 100 mmHg to about 400 mmHg, about 110 mmHg to about 120 mmHg, about 110 mmHg to about 130 mmHg, about 110 mmHg to about 140 mmHg, about 110 mmHg to about 150 mmHg, about 110 mmHg to about 175 mmHg, about 110 mmHg to about 200 mmHg, about 110 mmHg to about 225 mmHg, about 110 mmHg to about 250 mmHg, about 110 mmHg to about 300 mmHg, about 110 to about 350 mmHg, about 110 mmHg to about 400 mmHg, about 120 mmHg to about 130 mmHg, about 120 mmHg to about 140 mmHg, about 120 mmHg to about 150 mmHg, about 120 mmHg to about 175 mmHg, about 120 mmHg to about 200 mmHg, about 120 mmHg to about 225 mmHg, about 120 mmHg to about 250 mmHg, about 120 mmHg to about 300 mmHg, about 120 to about 350 mmHg, about 120 mmHg to about 400 mmHg, about 130 mmHg to about 140 mmHg, about 130 mmHg to about 150 mmHg, about 130 mmHg to about 175 mmHg, about 130 mmHg to about 200 mmHg, about 130 mmHg to about 225 mmHg, about 130 mmHg to about 250 mmHg, about 130 mmHg to about 300 mmHg, about 130 to about 350 mmHg, about 130 mmHg to about 400 mmHg, about 140 mmHg to about 150 mmHg, about 140 mmHg to about 175 mmHg, about 140 mmHg to about 200 mmHg, about 140 mmHg to about 225 mmHg, about 140 mmHg to about 250 mmHg, about 140 mmHg to about 300 mmHg, about 140 to about 350 mmHg, about 140 mmHg to about 400 mmHg, about 150 mmHg to about 175 mmHg, about 150 mmHg to about 200 mmHg, about 150 mmHg to about 225 mmHg, about 150 mmHg to about 250 mmHg, about 150 mmHg to about 300 mmHg, about 150 to about 350 mmHg, about 150 mmHg to about 400 mmHg, about 175 mmHg to about 200 mmHg, about 175 mmHg to about 225 mmHg, about 175 mmHg to about 250 mmHg, about 175 mmHg to about 300 mmHg, about 175 to about 350 mmHg, about 175 mmHg to about 400 mmHg, about 200 mmHg to about 225 mmHg, about 200 mmHg to about 250 mmHg, about 200 mmHg to about 300 mmHg, about 200 to about 350 mmHg, about 200 mmHg to about 400 mmHg, about 225 mmHg to about 250 mmHg, about 225 mmHg to about 300 mmHg, about 225 to about 350 mmHg, about 225 mmHg to about 400 mmHg, about 275 mmHg to about 300 mmHg, about 275 to about 350 mmHg, about 275 mmHg to about 400 mmHg, about 300 mmHg to about 325 mmHg, about 300 to about 350 mmHg, about 300 mmHg to about 400 mmHg, about 325 mmHg to about 350 mmHg, about 325 to about 375 mmHg, about 325 mmHg to about 400 mmHg, about 350 mmHg to about 375 mmHg, about 350 to about 400 mmHg, or about 375 mmHg to about 400 mmHg.

The breast milk distribution system (1) may pump from about 1 second to about 2 hours, about e.g., about 30 seconds to about 1 minute, about 30 seconds to about 2 minutes, about 30 seconds to about 3 minutes, about 30 seconds to about 4 minutes, about 30 seconds to about 5 minutes, about 30 seconds to about 10 minutes, about 30 seconds to about 15 minutes, about 30 seconds to about 30 minutes, about 30 seconds to about 5 minutes, about 5 minutes to about 10 minutes, about 5 minutes to about 15 minutes, about 5 minutes to about 20 minutes, about 5 minutes to about 25 minutes, about 5 minutes to about 30 minutes, about 5 minutes to about 35 minutes, about 5 minutes to about 40 minutes, about 5 minutes to about 1 hour, about 10 minutes to about 15 minutes, about 10 minutes to about 20 minutes, about 10 minutes to about 25 minutes, about 10 minutes to about 30 minutes, about 10 minutes to about 40 minutes, about 10 minutes to about 50 minutes, about 10 minutes to about 1 hour, about 15 minutes to about 30 minutes, about 15 minutes to about 45 minutes, about 15 minutes to about 1 hour, about 15 minutes to about 1.25 hours, about 15 minutes to about 1.5 hours, about 15 minutes to about 1.75 hours, about 15 minutes to about 2 hours, about 20 minutes to about 30 minutes, about 20 minutes to about 40 minutes, about 20 minutes to about 50 minutes, about 30 minutes to about 45 minutes, about 30 minutes to about 1 hour, about 30 minutes to about 1.25 hours, about 30 minutes to about 1.5 hours, about 30 minutes to about 1.75 hours, about 30 minutes to about 2 hours, about 45 minutes to about 1 hour, about 45 minutes to about 1.25 hours, about 45 minutes to about 1.5 hours, about 45 minutes to about 1.75 hours, about 45 minutes to about 2 hours, about 1 hour to about 1.25 hours, about 1 hour to about 1.5 hours, about 1 hour to about 1.75 hours, about 1 hour to about 2 hours, about 1.25 hours to about 1.5 hours, about 1.25 hours to about 1.75 hours, about 1.25 hours to about 2 hours, about 1.5 hours to about 1.75 hours, about 1.5 hours to about 2 hours, or about 1.75 hours to about 2 hours. The user may input a pump program from about 1 second to about 2 hours, and, e.g., set the program before the start of an activity, rest, or sleep.

In some embodiments, the method further includes turning on a positive pressure source. A positive pressure source may be turned on after the breast cup (2) contacts the human breast. In some embodiments, the positive pressure source is turned on with the power switch (14). In some embodiments, the positive pressure source is turned on remotely. In some embodiments, the positive pressure source is turned on automatically according to a pre-programmed schedule. In some embodiments, the positive pressure source is turned on automatically according to a pre-programmed schedule a plurality of times.

In some embodiments, the method further includes turning off the breast milk distribution system (1). In some embodiments, the breast milk distribution system (1) is turned off with the power switch (14). In some embodiments, the breast milk distribution system (1) is turned off remotely. In some embodiments, the breast milk distribution system (1) is turned off automatically according to a pre-programmed schedule. In some embodiments, the breast milk distribution system (1) is turned off automatically according to a pre-programmed schedule a plurality of times.

In some embodiments, the method further includes turning off the negative pressure source (9). In some embodiments, the negative pressure source (9) is turned off with the power switch (14). In some embodiments, the negative pressure source (9) is turned off remotely. In some embodiments, the negative pressure source (9) is turned off automatically according to a pre-programmed schedule. In some embodiments, the negative pressure source (9) is turned off automatically according to a pre-programmed schedule a plurality of times.

The method may include alternating between a first pressure to extend the nipple and express milk, and a second pressure to contact the nipple and slow or stop milk expression. Additionally, the method may include pumping at from two to ten pressures, e.g., one, two, three, four, five, six, seven, eight, nine, or ten pressures. The pressures applied to the breast may increase or decrease throughout the pumping.

In some embodiments, the method includes placing an ice pack in the enclosure (4). In some embodiments, the method includes removing the ice pack from the enclosure (4). In some embodiments, the method includes placing the ice pack in a freezer.

As discussed above, the breast milk distribution system (1) may include at least one sensor. The method may further include the taking of a weight, temperature, pressure, pH, viscosity, optical, volume, or flow measurement. The method may further include alerting a user of a sensor measurement. The method may further include changing at least one of the first pressure or second pressure based on the temperature, pressure, or flow measurement.

The disclosure further provides methods of cleaning a breast milk distribution system (1), including providing a cleaning fluid to breast cup (2); and pumping the cleaning fluid from the breast cup (2) to the reservoir (3) or waste.

The present invention provides a method of distributing milk from breast pumping, including: (i) providing the breast milk distribution system (1) of the present disclosure; (ii) pumping a human breast to induce milk from a first breast pumping session to flow from a nipple to the manifold (6) via the breast cup (2); (iii) providing fluidic communication between the inlet (8) of the manifold (6) and a first reservoir (3) to allow milk from the first breast pumping session to flow into the first reservoir (3); (iv) removing fluidic communication between the inlet (8) of the manifold (6) and the first fluid reservoir (3); (v) pumping the human breast to induce milk from a second breast pumping session to flow from the nipple to the manifold (6) via the breast cup (2); and (vi) providing fluidic communication between the inlet (8) of the manifold (6) and a second reservoir (3) to allow milk from the second breast pumping session to flow into the second reservoir (3).

In some embodiments, providing fluidic communication between the inlet (8) of the manifold (6) and the first reservoir (3) includes opening a first valve (24). In some embodiments, the control unit sends a signal to the first valve (24) to open and/or close. In some embodiments, the control unit sends a signal to the second valve (24) to open and/or close.

In some embodiments, the time between step (ii) and step (v) is from about 30 minutes to about 240 minutes (e.g., 30 minutes to 60 minutes, 30 minutes to 90 minutes, 60 minutes to 90 minutes, about minutes to about 120 minutes, about 60 minutes to about 180 minutes, about 90 minutes to about 180 minutes, about 90 minutes to about 240 minutes, or about 120 minutes to about 240 minutes). In some embodiments, the method further includes (vi) removing fluidic communication between the inlet (8) of the manifold (6) and the second fluid reservoir (3); and (vii) providing fluidic communication between the inlet (8) of the manifold (6) and a third reservoir (3); and (viii) pumping the human breast to induce milk from a third breast pumping session to flow from the nipple to the manifold (6) via the breast cup (2). In some embodiments, the time between step (v) and step (viii) is from 30 minutes to 240 minutes.

In some embodiments, the method further includes providing fluidic communication between (i) the inlet (8) of the manifold (6) and (ii) the first reservoir (3), the second reservoir (3), or the third fluid reservoir (3) by moving, e.g., rotating, the movable, e.g., rotating, member. In some embodiments, the method further includes removing fluidic communication between (i) the inlet (8) of the manifold (6) and (ii) the first reservoir (3), the second reservoir (3), or the third fluid reservoir (3) by moving, e.g., rotating, the movable, e.g., rotating, member.

In some embodiments, the method further includes providing fluidic communication between (i) the inlet (8) of the manifold (6) and (ii) the first reservoir (3), the second reservoir (3), or the third fluid reservoir (3) by opening the valve (24) to the inlet of the first reservoir (3), the second reservoir (3), or the third fluid reservoir (3). In some embodiments, the method further includes removing fluidic communication between (i) the inlet (8) of the manifold (6) and (ii) the first reservoir (3), the second reservoir (3), or the third fluid reservoir (3) by closing the valve (24) to the inlet of the first reservoir (3), the second reservoir (3), or the third fluid reservoir (3).

In some embodiments, the method further includes providing fluidic communication between (i) the inlet (8) of the manifold (6) and (ii) the first reservoir (3), the second reservoir (3), or the third fluid reservoir (3) by moving the arm. In some embodiments, the method further includes removing fluidic communication between (i) the inlet (8) of the manifold (6) and (ii) the first reservoir (3), the second reservoir (3), or the third fluid reservoir (3) by moving the arm. In some embodiments, the method further includes moving the arm with the drive unit (11), wherein the drive unit (11) is the stepper motor.

In some embodiments, a subject including the human breast is moving, reclining, resting, or sleeping.

Kits

In another aspect, the disclosure provides kits. Kits may include two or more unconnected components of a breast milk distribution system. A kit may include any two or more, e.g., all, of a manifold, fluid conduit, reservoir, reservoir enclosure, pressure source, and breast cup.

EXAMPLES

Example 1

A breast milk distribution system is shown in FIGS. 5A-5B. The breast milk distribution system (1) includes an inlet to connect to a fluid conduit (5) from a breast cup (2). The inlet is fluidly connected to an alignment plate (17) having an outlet (13). The alignment plate is rotated between four inlets in a manifold. The manifold has four arms and is made up of top and bottom plates sealed with a gasket (20). The bottom plate includes four channels, each terminating at an outlet. The outlet includes an O-ring on the exterior to mate with the inlet to a reservoir, e.g., milk bottle. A stepper motor (10) connected to a drive dog (21) rotates the alignment plate between the inlets in the manifold. The milk distribution system further includes a vertical body (19) to support the inlet (8), alignment plate (17), manifold (6), motor (10), and drive dog (21). The milk distribution system also includes a weighing plate (18) on which up to four reservoirs may rest. The base also includes a weight sensor to measure the weight on the weighing plate. The milk distribution system further includes a stationary base (22) to support the other components.

Milk is delivered via the inlet to the alignment plate, the outlet of which is aligned with one of the four inlets of the manifold. Milk then flows through the channel in the manifold and into a reservoir. The weight sensor can be used to determine the amount of milk delivered to a reservoir. Once a pumping cycle is complete, the system may rotate the alignment to the next, empty reservoir or to an intermediate position between manifold inlets. Reservoirs are sealed when the alignment plate is not aligned with the manifold inlet to which it is connected.

Example 2

Figure 6:
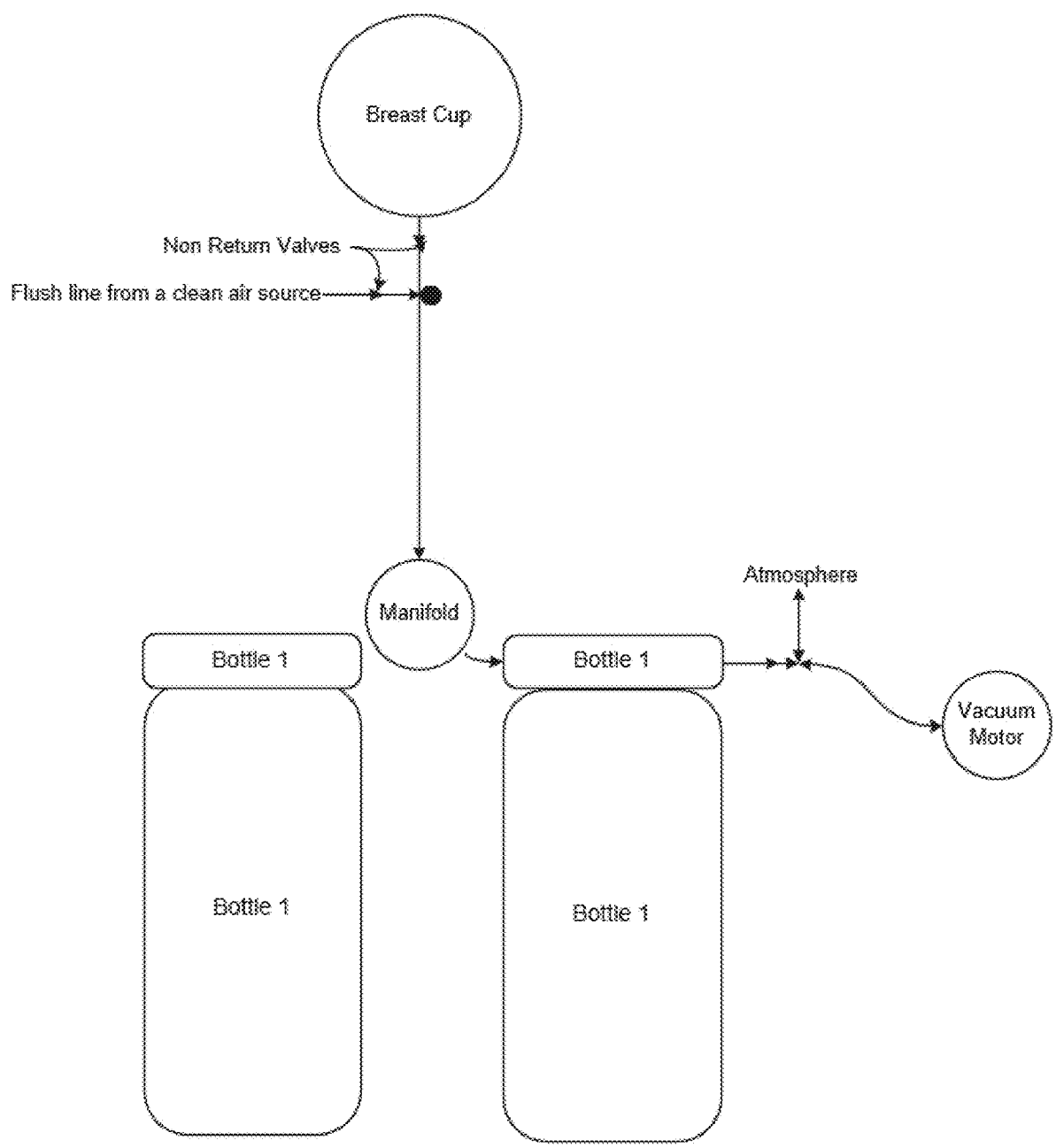
FIG. 6 shows a schematic of a breast milk distribution system (1) with a flush line and negative pressure source.

FIG. 6 shows a breast milk distribution system (1) that includes a flush line connected to a fluid conduit (5). One directional valves prevent back flow when either milk or flush air is being drawn into the conduit. The manifold (6) connects to one of the reservoirs (3). A vacuum reduces pressure in the reservoir (3) being filled. A vent may be present to release vacuum when the flush is complete.

Other embodiments are in the claims.

What is claimed is:

1. A breast milk distribution system, comprising:
   a manifold configured to be in fluidic communication with a breast cup, wherein the manifold comprises an inlet, a plurality of outlets, and a drive unit configured to move the inlet or the plurality of outlets; and
   a reservoir enclosure for housing a plurality of reservoirs, wherein each reservoir of the plurality of reservoirs is configured to be in fluidic communication with a different outlet of the plurality of outlets.

2. The breast milk distribution system of claim 1, further comprising the plurality of reservoirs.

3. The breast milk distribution system of claim 2, wherein the plurality of reservoirs is from 2 to 12 reservoirs.

4. The breast milk distribution system of claim 1, further comprising a pressure source in fluidic communication with the manifold and/or at least one of the plurality of reservoirs.

5. The breast milk distribution system of claim 1, wherein the manifold comprises a straight manifold, a right-angle manifold, a round manifold, a block manifold, a square manifold, a hex manifold, a wye manifold, or a rotating joint manifold.

6. The breast milk distribution system of claim 1, wherein the manifold comprises a movable member comprising the inlet of the manifold and a stationary member comprising the plurality of outlets of the manifold; wherein the movable member is configured to move and place the inlet in fluidic communication with one of the plurality of outlets at a time.

7. The breast milk distribution system of claim 6, wherein the movable member rotates.

8. The breast milk distribution system of claim 1, wherein each of the plurality of outlets comprises a valve.

9. The breast milk distribution system of claim 8, wherein the drive unit is configured to open and close the valve.

10. The breast milk distribution system of claim 1, further comprising a fluid conduit configured to provide fluidic communication between the breast cup and the inlet of the manifold.

11. The breast milk distribution system of claim 10, wherein the fluid conduit comprises a first one directional valve and an intersecting flush line having a second one directional therein, wherein the first one directional valve prevents backflow from the flush line and the second one directional valve prevents backflow from the fluid conduit.

12. The breast milk distribution system of claim 1, wherein the reservoir enclosure comprises a lid.

13. The breast milk distribution system of claim 12, wherein the manifold is disposed in the lid of the reservoir enclosure.

14. The breast milk distribution system of claim 1, further comprising a pressure source.

15. The breast milk distribution system of claim 1, wherein the enclosure comprises insulation.

16. The breast milk distribution system of claim 1, further comprising the breast cup in fluidic communication with the inlet of the manifold.

17. The breast milk distribution system of claim 1, wherein the reservoir enclosure further comprises a weight sensor configured to measure the weight of one or more of the plurality of reservoirs.

18. The breast milk distribution system of claim 1, wherein the inlet is disposed in an alignment plate, the motion of which provides fluidic communication between the inlet and only one of the plurality of outlets.

19. The breast milk distribution system of claim 1, wherein the drive unit is an integral drive unit of the manifold.

* * * * *